United States Patent
Jalce et al.

(10) Patent No.: US 10,160,732 B2
(45) Date of Patent: Dec. 25, 2018

(54) MIF INHIBITORS

(71) Applicants: MIFCARE, Paris (FR); Gael Jalce, Saint-Michel-sur-Orge (FR)

(72) Inventors: Gael Jalce, Saint-Michel-sur-Orge (FR); Bernardin Akagah, Massy (FR)

(73) Assignees: MIFCARE, Paris (FR); Gael Jalce, Saint-Michel-sur-Orge (FR)

( * ) Notice: Subject to any disclaimer, the term of this patent is extended or adjusted under 35 U.S.C. 154(b) by 34 days.

(21) Appl. No.: 15/302,648

(22) PCT Filed: Apr. 10, 2015

(86) PCT No.: PCT/EP2015/057907
§ 371 (c)(1),
(2) Date: Oct. 7, 2016

(87) PCT Pub. No.: WO2015/155358
PCT Pub. Date: Oct. 15, 2015

(65) Prior Publication Data
US 2017/0029387 A1 Feb. 2, 2017

(30) Foreign Application Priority Data
Apr. 10, 2014 (EP) .................................. 14164210

(51) Int. Cl.
C07D 263/58 (2006.01)
C07D 413/06 (2006.01)
A61K 31/423 (2006.01)
C07D 235/28 (2006.01)

(52) U.S. Cl.
CPC ......... C07D 263/58 (2013.01); C07D 235/28 (2013.01); C07D 413/06 (2013.01)

(58) Field of Classification Search
None
See application file for complete search history.

(56) References Cited

U.S. PATENT DOCUMENTS 3,669,672 A 6/1972 Shiba et al.
2005/0267148 A1 12/2005 Tsuchiya et al.

FOREIGN PATENT DOCUMENTS

| CA | 2014492 A1 | 10/1990 |
| JP | 51151134 A | 12/1976 |
| WO | 8802749 | 4/1988 |
| WO | 2010021693 A2 | 2/2010 |
| WO | 2015155358 A1 | 10/2015 |

OTHER PUBLICATIONS

Aliev, et al., Agrokhimiya, 9:118 (Abstract only) (Year: 1991).*
STN/CAS Database Registry No. RN 354793-13-8. (Year: 2001).*
STN/CAS Database Registry No. RN 286008-69-3 (Year: 2000).*
STN/CAS Database Registry No. RN 1392273-83-4 (Year: 2012).*
Jodi B. Lubetsky, et al., Enzyme Catalysis and Regulation: The Tautomerase Active Site of Macrophage Migration Inhibitory Factor Is a Potential Target for Discovery of Novel Anti-inflammatory Agents, The Journal of Biological Chemistry, Jul. 12, 2002, pp. 24976-24982, vol. 277, No. 28.
Yousef Al-Abed, et al., ISO-1 Binding to the Tautomerase Active Site of MIF Inhibits Its Pro-inflammatory Activity and Increases Survival in Severe Sepsis, The Journal of Biological Chemistry, Nov. 4, 2005, pp. 36541-36544, vol. 280, No. 44.
Katherine L. Meyer-Siegler, et al., Inhibition of Macrophage Migration Inhibitory Factor or Its Receptor (CD74) Attenuates Growth and Invasion of DU-145 Prostate Cancer Cells, The Journal of Immunology, 2006, pp. 8730-8739, vol. 177, No. 12.
Xini Zhang, et al., Inhibition of macrophage migration inhibitory factor (MIF) tautomerase activity by dopachrome analogs, Bioorganic & Medicinal Chemistry Letters, 1999, pp. 3193-3198, vol. 9, No. 22, Elsevier Science Ltd.
Zoe Cournia, et al., Discovery of Human Macrophage Migration Inhibitory Factor (MIF)-CD74 Antagonists via Virtual Screening, Journal of Medicinal Chemistry, 2009, pp. 416-424, vol. 52, No. 2.
Alissa A. Hare, et al., Optimization of N-benzyl-benzoxazol-2-ones as receptor antagonists of macrophage migration inhibitory factor (MIF), Bioorganic & Medicinal Chemistry Letters, 2010, pp. 5811-5814, vol. 20, Elsevier Ltd.
Lei Xu, et al., Current developments of macrophage migration inhibitory factor (MIF) inhibitors, Drug Discovery Today, Jun. 2013, pp. 592-600, vol. 18, Nos. 11/12, Elsevier Ltd.
Jun. 1, 2015, International Search Report issued for related International Application No. PCT/EP2015/057907.
Anna-Maria Monforte, et al., Novel $N_1$-substituted 1,3-dihydro-2H-benzimidazol-2-ones as potent non-nucleoside reverse transcriptase inhibitors, Bioorganic & Medicinal Chemistry, 2008, pp. 7429-7435, vol. 16, No. 15, Elsevier Ltd.
B. Rada, et al., Antiviral activity of benzothiazole and benzothiazolinethione derivatives in cell cultures, Acta Virologica, 1979, pp. 203-209, vol. 23, No. 3.
Maria C. Guimarães, et al., Computer-assisted design of dual-target anti-HIV-1 compounds, Medicinal Chemistry Research, 2014, pp. 1548-1558, vol. 23, No. 3, Springer Science+Business Media.
Surendra Kumar, et al., QSAR modeling of the inhibition of reverse transcriptase enzyme with benzimidazolone analogs, Medicinal Chemistry Research, 2011, pp. 1530-1541, vol. 20, No. 9, Springer Science+Business Media.
Marcus Freitag, et al., Synthesis and biological activity of splitomicin analogs targeted at human NAD-dependent histone deacetylases (sirtuins), Bioorganic & Medicinal Chemistry, 2011, pp. 3669-3677, vol. 19, No. 12, Elsevier Ltd.

(Continued)

*Primary Examiner* — Michael Barker
(74) *Attorney, Agent, or Firm* — Young & Thompson

(57) ABSTRACT

Compounds of Formula (I'), and the use of the compounds of Formula (I') as inhibitors of macrophage migration inhibitory factor (MIF). The use of compounds of Formula (I') or pharmaceutical compositions thereof and method of using them, for treating disorders, diseases or conditions related to MIF.

9 Claims, No Drawings

(56) References Cited

OTHER PUBLICATIONS

W. S. Hamama, Behaviour of 2,3-dihydro-1 H-benzo[d]imidazole-2-thione towards amines under Mannich-type condition, Journal of Chemical Research, 2000, pp. 269-271.
Masatoshi Yamato, et al., Synthesis of 3-substituted benzoxazoline-2-thiones, Chemical & Pharmaceutical Bulletin, 1983, pp. 1733-1737, vol. 31, No. 5.
Ahmed F. Abdel-Magid, et al., Reductive Amination of Aldehydes and Ketones with Sodium Triacetoxyborohydride. Studies on Direct and Indirect Reductive Amination Procedures, Journal of Organic Chemistry, 1996, pp. 3849-3862, vol. 61, No. 11.

\* cited by examiner

MIF INHIBITORS

FIELD OF INVENTION

The present invention provides compounds of Formula I:

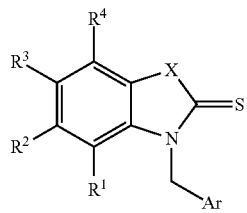

wherein X, $R^1$, $R^2$, $R^3$, $R^4$ and Ar are as defined below.

The present invention relates to the use of the compounds of Formula I as inhibitors of macrophage migration inhibitory factor (MIF). The invention also relates to the use of compounds of Formula I or pharmaceutical compositions thereof and method using thereof, for treating disorders, diseases or conditions related to MIF.

BACKGROUND OF INVENTION

Macrophage migration inhibitory factor (MIF) also known as glycosylation-inhibiting factor, L-dopachrome isomerase, or phenylpyruvate tautomerase is a highly conserved protein with pleiotropic actions. Discovered in the mid-1960s as a T cell cytokine that inhibited macrophage migration, its biochemical natures and its biological functions remained enigmatic for a long time. It is now well known that MIF (which exhibits tautomerase and oxidoreductase enzymatic activities) plays roles in cell growth, proliferation, and survival, as well as in leukocytic integrin activation, and induction of pro-inflammatory gene expression. In addition to MIF, a very recent study has identified a functional homologue of MIF with a similar genomic structure and expression patterns: the D-dopachrome tautomerase (DDT or MIF-2).

MIF and/or DDT are released upon stimulation by stress, endotoxin, inflammatory, and immune stimuli. Moreover MIF and/or DDT play an important, upstream role in the inflammatory cascade by promoting the release of other inflammatory cytokines (tumor necrosis factor (TNF)-α, interleukin (IL)-1, IL-6, IL-8, IL-12, interferon (IFN)-γ . . . ) and are potential therapeutic targets in multiple inflammatory, infectious, metabolic and autoimmune diseases including cancer. In patients with rheumatoid arthritis, MIF plays a central role in the activation of synoviocytes by increasing the expression of phospholipase A2, cyclooxygenase 2 (COX2), IL-6, IL-8, matrix metalloproteinase (MMP)-1 and MMP-3. In addition, MIF can modulate or "counter-balance" the anti-inflammatory and immunosuppressive effects of glucocorticoids on macrophages and T cells.

MIF and/or DDT bind to and activate CD74 and chemokine receptors CXCR2 and CXCR4. MIF signaling through CD74 occurs through two different modes: (a) in a CD44/Src dependent pathway in which CD74 interacts with CD44. CD44 is a transmembrane protein whose phosphorylation leads to activation of Src-family kinase and MAPK/ERK, PI3K/Akt and NF-κB pathway and to apoptotic resistance by increasing the anti-apoptotic factors BCL2, BCL-xL and by inhibiting p53; or (b) in a CD44 independent pathway in which CD74 cytosolic region is cleaved by a two-step process: translocation of CD74 cytosolic fragment (CD74-ICD) to the cell nucleus resulting in NF-κB activation, and induction of a survival cascade via up-regulation of BCL2. Moreover, CD74 is known to interact with angiotensin AT1-receptor and nitric-oxide synthase 2.

MIF is also implicated in multiple aspects of growth including control of cell proliferation and promotion of angiogenesis; moreover, an important role of MIF has been reported in tumor genesis. The inhibition of MIF-CD74 binding has been shown to reduce tumor growth and angiogenesis.

Considering the implication of MIF in various important diseases, this protein represents an interesting therapeutic target.

Injectable biological agents such as anti-cytokine antibodies or soluble cytokine receptors have been shown to inhibit MIF activities. However, these strategies present some drawbacks such as high cost and inconvenience of application.

In the past few years, significant efforts have been made to develop small molecules to inactivate MIF tautomerase activity, assessed using in vitro binding assay for MIF with CD74. Among identified products of interest, a prototypical MIF inhibitor (ISO-1) has been described and was shown to be active in vitro and in vivo:

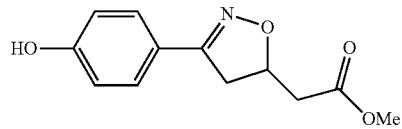 [SMILES: COC(=O)CC1CC(c2ccc(O)cc2)=NO1]

However, ISO-1 has shown only micromolar potency and off-target effects have also been reported, limiting its usefulness (Lubetsky et al., J. Biol. Chem., 2002, 277(28), 24976-24982; Al-Abed et al., J. Biol. Chem., 2005, 280(44), 36541-36544; Meyer-Siegler et al., J. Immunol, 2006, 177 (12), 8730-8739).

In 1999, Zhang and Bucala found that a group of dopachrome analogs could inhibit the tautomerase activity of MIF at concentrations tenfold less than substrates (Zhang and Bucala, Bioorg. Med. Chem. Lett., 1999, 9(22), 3193-3198).

MIF modulators are also disclosed in WO2010/021693, especially N-benzyl-benzoxazol-2-one compounds of general formula (i)

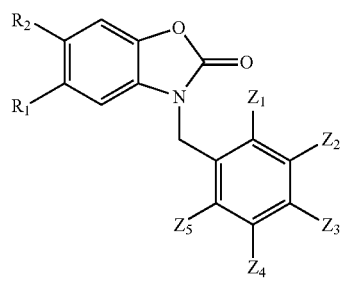

wherein $R_1$ and $R_2$ represent preferably H, $CH_3$, $OCH_3$, $CH_2OH$, F, or OH and $Z_1$, $Z_2$, $Z_3$, $Z_4$ and $Z_5$ represent preferably H or $OCH_3$.

This kind of N-benzyl-benzoxazol-2-ones is also reported as MIF antagonists in Cournia et al., J. Med. Chem., 2009, 52, 416-424; Hare et al., Bioorg. Med. Chem. Lett., 2010, 20, 5811-5814; Xu et al., Drug Discov. Today, 2013, 18(11-12), 592-600.

The prior art molecules may not provide an optimized inhibition of MIF tautomerase activity.

Thus, substantial work remains to be done to provide new, better-tolerated and more powerful therapeutic small molecules to inhibit MIF tautomerase activity.

The Applicant surprisingly evidenced that isosteres of above N-benzyl-benzoxazol-2-ones have superior MIF inhibitory effects compared to current known MIF inhibitors. Especially, the Applicant hereby provides compounds of Formula I

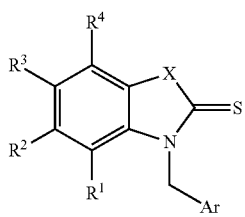

wherein X, Ar, $R^1$, $R^2$, $R^3$ and $R^4$ are as defined below.

Compounds of Formula I are more selective and demonstrate significant biological improvements, relative to ISO-1 or benzoxazol-2-ones reported above.

Definitions

In the present invention, the following terms have the following meanings:

"alkyl" by itself or as part of another substituent refers to a hydrocarbyl radical of Formula $C_nH_{2n+1}$, wherein n is a number greater than or equal to 1. Generally, alkyl groups of this invention comprise from 1 to 6 carbon atoms. Alkyl groups may be linear or branched and may be substituted as indicated herein. Examples of alkyl groups are methyl, ethyl, n-propyl, i-propyl, butyl and its isomers (e.g. n-butyl, i-butyl and t-butyl); pentyl and its isomers, hexyl and its isomers.

"alkenyl" refers to unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

"alkynyl" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers—and the like.

"alkoxy" refers to any O-alkyl group.

"alkylthio" refers to any S-alkyl group.

"aryl" refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1 (2H)-yl, 6-oxo-pyrudazin-1 (6H)-yl, 2-oxopyridin-1 (2H)-yl, 1,3-benzodioxolyl, quinolinyl, isoquinolinyl, cinnolinyl, quinazolinyl, quinoxalinyl.

"alkylaryl" refers to any group alkyl-aryl-.

"alkylheteroaryl" refers to any group alkyl-heteroaryl-.

"halo" refers to fluoro, chloro, bromo, iodo.

"haloalkyl" refers to any group alkyl group substituted by one or more halo group. Examples of preferred haloalkyl groups are $CF_3$, $CHF_2$ and $CH_2F$.

"hydroxyalkyl" refers to any alkyl group substituted by at least one hydroxyl group.

"cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl.

"heterocyclyl" or "heterocycle" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulf oxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

"amino" refers to any compound derived from ammoniac $NH_3$ by substitution of one or more hydrogen atoms with an organic radical. Amino preferably refers to $—NH_2$, —NHR and —NRR' wherein R and R' are preferably alkyl groups. Therefore "amino" includes monoalkylamino and dialkylamino groups.

"amide" refers to a group —CO—NH—R or —NH—CO—R wherein R represents preferably an alkyl group, as defined above.

"aminoacid" refers to a group —O—CO—CHR—$NH_2$ or —NH—CHR—CO—OH wherein R represent the lateral chain of the aminoacid, preferably the lateral chain of a natural aminoacid.

"carbamate" refers to a group —O—CO—NRR' or —NR—CO—OR' wherein R and R' represent preferably each independently alkyl groups.

"carbamide" refers to a group —NR—CO—NR'R" wherein R, R' and R" represent preferably each independently alkyl groups.

"carbonate" refers to a group —O—CO—OR wherein R represents preferably an alkyl group.

"ester" refers to a group —O—CO—R or —CO—OR wherein R represents preferably an alkyl group.

"thioester" refers to a group —S—CO—R or —CO—SR wherein R represents preferably an alkyl group.

"phosphonate" refers to a group —O—PO(OR)$_2$ wherein R represents H, alkyl, Na or Ca.

"phosphonate methyloxy" refers to a group —O—$CH_2$—O—PO(OR)$_2$ wherein R represents H, alkyl, Na or Ca.

"phosphonate methylamino" refers to a group —NH—$CH_2$—O—PO(OR)$_2$ wherein R represents H, alkyl, Na or Ca.

"sulfonamide" refers to a group —$SO_2$—NRR' or —NR—$SO_2$—R' wherein R and R' represent preferably each independently alkyl groups.

"solvate" is used herein to describe a molecular complex comprising the compound of the invention and one or more pharmaceutically acceptable solvent molecules, for example, ethanol.

"subject" refers to a warm-blooded animal, more preferably a human. Preferably, the subject is a patient, i.e. the subject is awaiting the receipt of, or is receiving medical care or is/will be the object of a medical procedure.

"human" refers to a subject of both genders and at any stage of development (i.e. neonate, infant, juvenile, adolescent, adult).

"treatment", "treat" and "treating" refers to therapeutic treatment, prophylactic or preventative measures and deferment of the disease onset; wherein the object is to delay, prevent or slow down (lessen) the targeted pathologic condition or disorder. Those in need of treatment include those already affected with a disease or a condition, as well as those prone to develop a disease or a condition, or those in whom a disease or a condition is to be prevented or delayed. A subject is successfully "treated" for a disease or a condition if, after receiving a therapeutic amount of a composition according to the invention, the subject shows observable and/or measurable inflammation decrease, and/or arterial pressure decrease and/or cell proliferation decrease and/or improvement in quality of life issues. The above parameters for assessing successful treatment and improvement in the disease are readily measurable by routine procedures familiar to the skilled artisan.

The term "therapeutically effective amount" (or more simply an "effective amount") as used herein means the amount of active agent or active ingredient that is sufficient to achieve the desired therapeutic or prophylactic effect in the subject to which/whom it is administered.

The term "administration", or a variant thereof (e.g. "administering"), means providing the active agent or active ingredient, alone or as part of a pharmaceutically acceptable composition, to the subject in whom/which the condition, symptom, or disease is to be treated or prevented.

By "pharmaceutically acceptable" is meant that the ingredients of a pharmaceutical composition are compatible with each other and not deleterious to the subject thereof.

By "pharmaceutically acceptable carrier" is meant that a carrier that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by FDA Office of Biologics standards.

The term "MIF" refers to macrophage migration inhibitory factor or active fragment thereof. An active fragment of MIF may comprise a fragment of a portion of the MIF protein harboring the tautomerase enzymatic activity, or a fragment that is capable of binding to one of its receptors.

"inhibitor of MIF" refers to any agent that attenuates, inhibits, opposes, counteracts, or decreases the biological activity of MIF. A MIF antagonist may be an agent that inhibits or neutralizes MIF activity (including, without limitation, small molecules and anti-MIF antibodies); an agent that prevents the binding of MIF to CD74 (including, without limitation, an anti-CD74 antibody or an anti-MIF antibody or a fragment thereof); an agent that prevents the interaction between CD74 and CD44 (such as an anti-CD74 antibody or an anti-CD44 antibody or a fragment thereof); or an agent that prevents the interaction between CD74 and CD44. In one embodiment, the inhibitor of MIF is an inhibitor of MIF CD74 axis, preferably an inhibitor of MIF CD74 pathway, wherein the term MIF CD74 pathway refers to a multi-step biochemical pathway. Each step in this pathway, as in many biochemical pathways, not only passes information downstream but also receives feedback from messengers produced later in the pathway to either enhance or suppress earlier steps in the pathway. According to a specific embodiment, the inhibitor of MIF of the invention inhibits MIF binding to CD74 and CXCRs (including CXCR2, CXCR4 and/or CXCR7).

"biological function of MIF" refers to the ability of MIF to carry out one or more of the biological functions of MIF including, but not limited to, sustaining immune cell survival or activation, promoting cytokine promotion, down-regulating CCR5, binding to CD74, activating MAP kinase and Src signaling (e.g., ERK1/2, JNK, PI3K, and SAPK MAP kinase signaling), inhibiting p53, acting as a tautomerase, and/or acting as a thiol reductase.

DETAILED DESCRIPTION

Compound

This invention relates to a compound of general Formula I

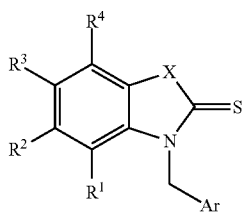

and pharmaceutically acceptable enantiomers, salts or solvates thereof, wherein:

X represents O, S or N—$R^5$, wherein $R^5$ represents a hydrogen atom or a group selected from alkyl, alkenyl, alkynyl, alkylaryl, alkylheteroaryl, —$COR^6$ wherein $R^6$ is a group selected from alkyl, alkenyl, alkynyl, alkoxy, aryl and heteroaryl; preferably X represents O;

Ar represents aryl or heteroaryl group, preferably selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzo-thiazolamine; optionally substituted by or more substituents selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone; preferably optionally substituted by or more substituents selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone; preferably Ar represents an optionally substituted phenyl group;

$R^1$-$R^4$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^4$ represent hydrogen, alkyl, cycloalkyl or haloalkyl, more preferably hydrogen, methyl or $CF_3$;

provided that compound of Formula I is not:

3-benzylbenzo[d]oxazole-2(3H)-thione;

3-(4-(dimethylamino)benzyl)benzo[d]oxazole-2(3H)-thione;

3-(2,4-dimethoxybenzyl)benzo[d]oxazole-2(3H)-thione;

3-(furan-2-ylmethyl)benzo[d]oxazole-2(3H)-thione;

5-chloro-3-(thiophen-2-ylmethyl)benzo[d]oxazole-2(3H)-thione;

5-chloro-3-(furan-2-ylmethyl)benzo[d]oxazole-2(3H)-thione;

3-(thiophen-2-ylmethyl)benzo[d]oxazole-2(3H)-thione;

3-(3,5-di-tert-butyl-4-hydroxybenzyl)benzo[d]thiazole-2(3H)-thione;

3-(5-(tert-butyl)-4-hydroxy-2-methylbenzyl)benzo[d]thiazole-2(3H)-thione;

3-(4-hydroxy-5-isopropyl-2-methylbenzyl)benzo[d]thiazole-2(3H)-thione;

3-(3-(tert-butyl)-2-hydroxy-5-methylbenzyl)benzo[d]thiazole-2(3H)-thione;

3-(3-allyl-4-hydroxy-5-methylbenzyl)benzo[d]thiazole-2(3H)-thione;

3-(4-hydroxy-3,5-diisopropylbenzyl)benzo[d]oxazole-2(3H)-thione;

3-(3,5-di-tert-butyl-4-hydroxybenzyl)benzo[d]oxazole-2(3H)-thione;

3-((2'-hydroxy-[1,1':3',1''-terphenyl]-5'-yl)methyl)benzo[d]oxazole-2(3H)-thione;

3-(3-(tert-butyl)-4-hydroxy-5-methylbenzyl)benzo[d]oxazole-2(3H)-thione;

3-(4-hydroxy-2,3,5-trimethylbenzyl)benzo[d]oxazole-2(3H)-thione;

3-(3,5-di-tert-butyl-2-hydroxybenzyl)benzo[d]oxazole-2(3H)-thione;

3-(2-hydroxy-3,5-dimethylbenzyl)benzo[d]oxazole-2(3H)-thione;

3-((4'-hydroxy-[1,1':3',1''-terphenyl]-5'-yl)methyl)benzo[d]oxazole-2(3H)-thione.

According to an embodiment, compounds of Formula I of the invention as described above, are of Formula I'

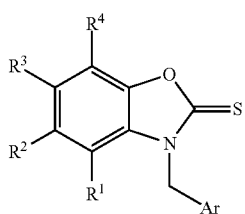

and pharmaceutically acceptable enantiomers, salts or solvates thereof, wherein:

Ar represents aryl or heteroaryl group, preferably selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzothiazolamine; optionally substituted by or more substituents selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone; preferably Ar represents an optionally substituted phenyl group;

$R^1$-$R^4$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^4$ represent hydrogen, alkyl, cycloalkyl or haloalkyl, more preferably hydrogen, methyl or $CF_3$;

provided that compound of Formula I' is not:
3-benzylbenzo[d]oxazole-2(3H)-thione;
3-(4-(dimethylamino)benzyl)benzo[d]oxazole-2(3H)-thione;
3-(2,4-dimethoxybenzyl)benzo[d]oxazole-2(3H)-thione;
3-(furan-2-ylmethyl)benzo[d]oxazole-2(3H)-thione;
5-chloro-3-(thiophen-2-ylmethyl)benzo[d]oxazole-2(3H)-thione;
5-chloro-3-(furan-2-ylmethyl)benzo[d]oxazole-2(3H)-thione;
3-(thiophen-2-ylmethyl)benzo[d]oxazole-2(3H)-thione;
3-(3,5-di-tert-butyl-4-hydroxybenzyl)benzo[d]thiazole-2(3H)-thione;
3-(5-(tert-butyl)-4-hydroxy-2-methylbenzyl)benzo[d]thiazole-2(3H)-thione;
3-(4-hydroxy-5-isopropyl-2-methylbenzyl)benzo[d]thiazole-2(3H)-thione;
3-(3-(tert-butyl)-2-hydroxy-5-methylbenzyl)benzo[d]thiazole-2(3H)-thione;
3-(3-allyl-4-hydroxy-5-methylbenzyl)benzo[d]thiazole-2(3H)-thione;
3-(4-hydroxy-3,5-diisopropylbenzyl)benzo[d]oxazole-2(3H)-thione;
3-(3,5-di-tert-butyl-4-hydroxybenzyl)benzo[d]oxazole-2(3H)-thione;
3-((2'-hydroxy-[1,1':3',1''-terphenyl]-5'-yl)methyl)benzo[d]oxazole-2(3H)-thione;
3-(3-(tert-butyl)-4-hydroxy-5-methylbenzyl)benzo[d]oxazole-2(3H)-thione;
3-(4-hydroxy-2,3,5-trimethylbenzyl)benzo[d]oxazole-2(3H)-thione;
3-(3,5-di-tert-butyl-2-hydroxybenzyl)benzo[d]oxazole-2(3H)-thione;
3-(2-hydroxy-3,5-dimethylbenzyl)benzo[d]oxazole-2(3H)-thione;
3-((4'-hydroxy-[1,1':3',1''-terphenyl]-5'-yl)methyl)benzo[d]oxazole-2(3H)-thione.

According to a specific embodiment, Ar is optionally substituted and is selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzothiazolamine. In a preferred embodiment, Ar is a phenyl group, optionally substituted. In one embodiment, when Ar is substituted, it is preferably substituted by one or more group selected from F, Cl, Br, $NO_2$, $NH_2$, $NMe_2$, OH, OMe, $CH_3$ or $CF_3$. In a specific embodiment, when Ar is substituted, it is preferably substituted by one or more group selected from OH, hydroxyalkyl, aminoacid, carbamate, carbonate, ester, thioester, phosphonate, phosphonate methyloxy, phosphonate methylamino, alkoxy and alkylthio.

According to a specific embodiment, Ar is a phenol group or a bio-isostere thereof, wherein preferred phenol bio-isosteres are selected from:

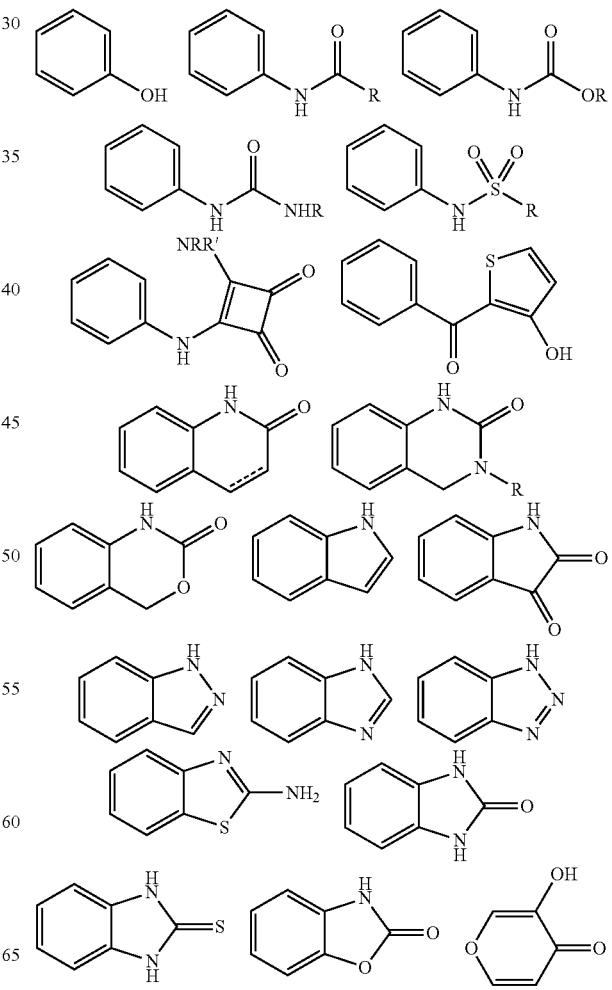

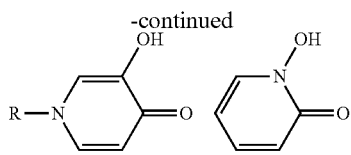

wherein R and R' are preferably selected from hydrogen, alkyl, cycloalkyl, alkenyl, alkynyl, aryl, heteroaryl, alkylaryl, alkylheteroaryl.

According to a specific embodiment, Ar is a phenol group or a prodrug thereof. Preferably, the prodrug of the phenol group is selected from aminoacid, carbamate, carbonate, ester, thioester, phosphonate, phosphonate methyloxy, phosphonate methylamino, alkyloxy and alkylthio groups.

According to a preferred embodiment, $R^1$ and $R^4$ represent hydrogen atoms. According to another preferred embodiment, $R^1$, $R^4$ and at least one of $R^2$ or $R^3$ represent hydrogen atoms. According to a specific embodiment, $R^1$, $R^3$ and $R^4$ represent hydrogen atoms and $R^2$ preferably represents an alkyl group, more preferably methyl. According to a specific embodiment, $R^1$, $R^3$ and $R^4$ represent hydrogen atoms and $R^2$ preferably represents a haloalkyl group, more preferably trifluoromethyl. According to another specific embodiment, $R^1$, $R^2$ and $R^4$ represent hydrogen atoms and $R^3$ preferably represents an alkyl group, more preferably methyl. According to another specific embodiment, $R^1$, $R^2$ and $R^4$ represent hydrogen atoms and $R^3$ preferably represents a haloalkyl group, more preferably trifluoromethyl.

According to an embodiment, compounds of Formula I of the invention as described above, including the proviso, are of Formula Ia:

and pharmaceutically acceptable enantiomers, salts or solvates thereof, wherein:
X, $R^2$ and $R^3$ are as defined in Formula I;
$Z^1$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^1$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^1$ represents H, F, Cl, Br, $NO_2$, $NH_2$, $NMe_2$, OH, OMe, $CH_3$ or $CF_3$;
$Z^2$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^2$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^2$ represents H, F, Cl, Br, $NO_2$, $NH_2$, $NMe_2$, OH, OMe, $CH_3$ or $CF_3$;
$Z^3$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^3$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^3$ represents H, F, Cl, Br, $NO_2$, $NH_2$, $NMe_2$, OH, OMe, $CH_3$ or $CF_3$;
$Z^4$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^4$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^4$ represents H, F, Cl, Br, $NO_2$, $NH_2$, $NMe_2$, OH, OMe, $CH_3$ or $CF_3$;

$Z^5$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^5$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^5$ represents H, F, Cl, Br, $NO_2$, $NH_2$, $NMe_2$, OH, OMe, $CH_3$ or $CF_3$;

provided that compound of Formula Ia is not:
3-benzylbenzo[d]oxazole-2(3H)-thione;
3-(4-(dimethylamino)benzyl)benzo[d]oxazole-2(3H)-thione;
3-(2,4-dimethoxybenzyl)benzo[d]oxazole-2(3H)-thione;
3-(furan-2-ylmethyl)benzo[d]oxazole-2(3H)-thione;
5-chloro-3-(thiophen-2-ylmethyl)benzo[d]oxazole-2(3H)-thione;
5-chloro-3-(furan-2-ylmethyl)benzo[d]oxazole-2(3H)-thione;
3-(thiophen-2-ylmethyl)benzo[d]oxazole-2(3H)-thione;
3-(3,5-di-tert-butyl-4-hydroxybenzyl)benzo[d]thiazole-2(3H)-thione;
3-(5-(tert-butyl)-4-hydroxy-2-methylbenzyl)benzo[d]thiazole-2(3H)-thione;
3-(4-hydroxy-5-isopropyl-2-methylbenzyl)benzo[d]thiazole-2(3H)-thione;
3-(3-(tert-butyl)-2-hydroxy-5-methylbenzyl)benzo[d]thiazole-2(3H)-thione;
3-(3-allyl-4-hydroxy-5-methylbenzyl)benzo[d]thiazole-2(3H)-thione;
3-(4-hydroxy-3,5-diisopropylbenzyl)benzo[d]oxazole-2(3H)-thione;
3-(3,5-di-tert-butyl-4-hydroxybenzyl)benzo[d]oxazole-2(3H)-thione;
3-((2'-hydroxy-[1,1':3',1''-terphenyl]-5'-yl)methyl)benzo[d]oxazole-2(3H)-thione;
3-(3-(tert-butyl)-4-hydroxy-5-methylbenzyl)benzo[d]oxazole-2(3H)-thione;
3-(4-hydroxy-2,3,5-trimethylbenzyl)benzo[d]oxazole-2(3H)-thione;
3-(3,5-di-tert-butyl-2-hydroxybenzyl)benzo[d]oxazole-2(3H)-thione;
3-(2-hydroxy-3,5-dimethylbenzyl)benzo[d]oxazole-2(3H)-thione;
3-((4'-hydroxy-[1,1':3',1''-terphenyl]-5'-yl)methyl)benzo[d]oxazole-2(3H)-thione.

According to an embodiment, compounds of Formula Ia of the invention as described above, are of Formula Ia':

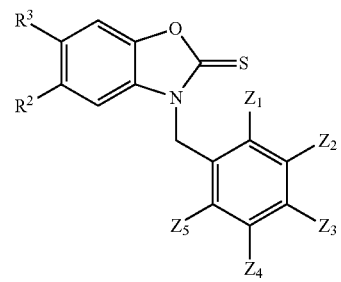

and pharmaceutically acceptable enantiomers, salts or solvates thereof, wherein:

$R^2$ and $R^3$ are as defined in Formula I;

$Z^1$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^1$ represents H, F, Cl, Br, $NO_2$, $NH_2$, $NMe_2$, OH, OMe, $CH_3$ or $CF_3$;

$Z^2$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^2$ represents H, F, Cl, Br, $NO_2$, $NH_2$, $NMe_2$, OH, OMe, $CH_3$ or $CF_3$;

$Z^3$ represents a hydrogen atom or a group selected from halo, hydroxyl hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^3$ represents H, F, Cl, Br, $NO_2$, $NH_2$, $NMe_2$, OH, OMe, $CH_3$ or $CF_3$;

$Z^4$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^4$ represents H, F, Cl, Br, $NO_2$, $NH_2$, $NMe_2$, OH, OMe, $CH_3$ or $CF_3$;

$Z^5$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^5$ represents H, F, Cl, Br, $NO_2$, $NH_2$, $NMe_2$, OH, OMe, $CH_3$ or $CF_3$;

provided that compound of Formula Ia' is not:
3-benzylbenzo[d]oxazole-2(3H)-thione;
3-(4-(dimethylamino)benzyl)benzo[d]oxazole-2(3H)-thione;
3-(2,4-dimethoxybenzyl)benzo[d]oxazole-2(3H)-thione;
3-(furan-2-ylmethyl)benzo[d]oxazole-2(3H)-thione;
5-chloro-3-(thiophen-2-ylmethyl)benzo[d]oxazole-2(3H)-thione;
5-chloro-3-(furan-2-ylmethyl)benzo[d]oxazole-2(3H)-thione;
3-(thiophen-2-ylmethyl)benzo[d]oxazole-2(3H)-thione;
3-(3,5-di-tert-butyl-4-hydroxybenzyl)benzo[d]thiazole-2(3H)-thione;
3-(5-(tert-butyl)-4-hydroxy-2-methylbenzyl)benzo[d]thiazole-2(3H)-thione;
3-(4-hydroxy-5-isopropyl-2-methylbenzyl)benzo[d]thiazole-2(3H)-thione;
3-(3-(tert-butyl)-2-hydroxy-5-methylbenzyl)benzo[d]thiazole-2(3H)-thione;
3-(3-allyl-4-hydroxy-5-methylbenzyl)benzo[d]thiazole-2(3H)-thione;
3-(4-hydroxy-3,5-diisopropylbenzyl)benzo[d]oxazole-2(3H)-thione;
3-(3,5-di-tert-butyl-4-hydroxybenzyl)benzo[d]oxazole-2(3H)-thione;
3-((2'-hydroxy-[1,1':3',1''-terphenyl]-5'-yl)methyl)benzo[d]oxazole-2(3H)-thione;
3-(3-(tert-butyl)-4-hydroxy-5-methylbenzyl)benzo[d]oxazole-2(3H)-thione;
3-(4-hydroxy-2,3,5-trimethylbenzyl)benzo[d]oxazole-2(3H)-thione;
3-(3,5-di-tert-butyl-2-hydroxybenzyl)benzo[d]oxazole-2(3H)-thione;
3-(2-hydroxy-3,5-dimethylbenzyl)benzo[d]oxazole-2(3H)-thione;
3-((4'-hydroxy-[1,1':3',1''-terphenyl]-5'-yl)methyl)benzo[d]oxazole-2(3H)-thione.

According to an embodiment, compounds of Formula Ia of the invention as described above, including the proviso, are of Formula Ib:

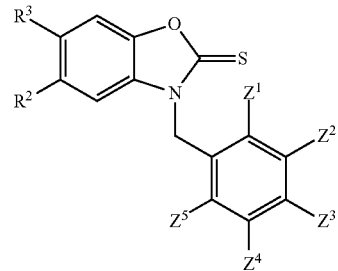

and pharmaceutically acceptable enantiomers, salts or solvates thereof, wherein $R^2$, $R^3$, $Z^1$, $Z^2$, $Z^3$, $Z^4$ and $Z^5$ are as defined in Formula Ia.

According to a specific embodiment, in compounds of Formula Ib, $R^3$ represents H.

According to a specific embodiment, in compounds of Formula Ib, $R^3$ represents an hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl; provided that $R^3$ is not methyl.

According to a specific embodiment, in compounds of Formula Ib, $R^2$ represents an alkyl group, preferably methyl, and $R^3$ represents a hydrogen atom. According to a specific embodiment, in compounds of Formula Ib, $R^2$ represents a haloalkyl group, preferably trifluoromethyl, and $R^3$ represents a hydrogen atom. According to a specific embodiment, in compounds of Formula Ib, $R^2$ and $R^3$ represents hydrogen atoms.

According to a specific embodiment, in compounds of Formula Ib, $Z^2$ represents a hydroxyl group. In this embodiment, $Z^1$, $Z^3$, $Z^4$ and $Z^5$ preferably represent hydrogen atoms. According to another specific embodiment, in compounds of Formula Ib, $Z^2$ represents a hydroxyl group and $Z^3$ represents a halogen, preferably a fluorine atom. In this embodiment, $Z^1$, $Z^4$ and $Z^5$ preferably represent hydrogen atoms.

According to an embodiment, compounds of Formula Ia of the invention as described above, including the proviso, are of Formula Ic:

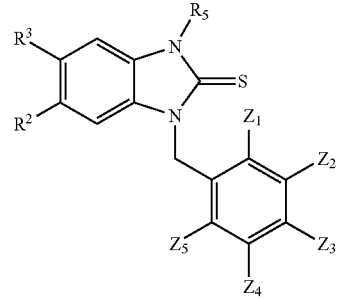

and pharmaceutically acceptable enantiomers, salts or solvates thereof, wherein $R^2$, $R^3$, $R^5$, $Z^1$, $Z^2$, $Z^3$, $Z^4$ and $Z^5$ are as defined in Formula Ia.

According to a specific embodiment, in compounds of Formula Ic, $R^5$ represents H.

According to an embodiment, compounds of Formula Ic of the invention as described above, including the proviso, are of Formula Ic-1 or Ic-2:

Ic-1

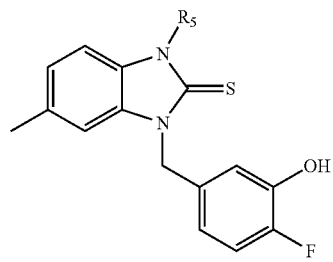

Ic-2

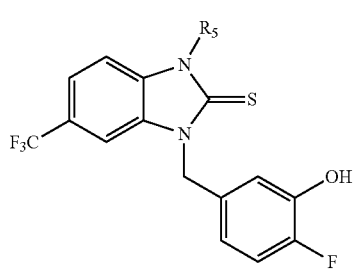

and pharmaceutically acceptable enantiomers, salts or solvates thereof, wherein $R^5$ is as defined in Formula Ia.

According to an embodiment, compounds of Formula Ia of the invention as described above, including the proviso, are of Formula Id:

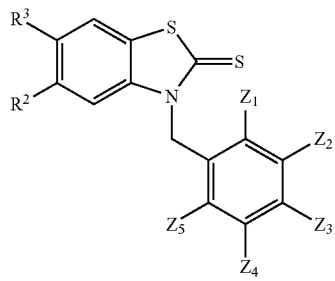

and pharmaceutically acceptable enantiomers, salts or solvates thereof, wherein $R^2$, $R^3$, $Z^1$, $Z^2$, $Z^3$, $Z^4$ and $Z^5$ are as defined in Formula Ia.

According to an embodiment, compounds of Formula Id of the invention as described above, including the proviso, are of Formula Id-1 or Id-2:

Id-1

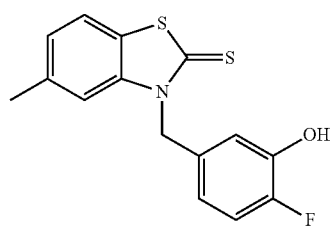

Id-2

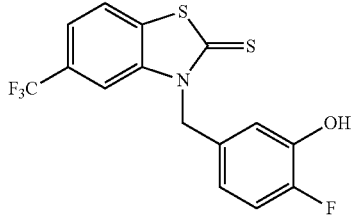

and pharmaceutically acceptable enantiomers, salts or solvates thereof, wherein $R^5$ is as defined in Formula Ia.

According to a preferred embodiment of the invention, compounds of Formula I of the invention are those listed in table 1 below:

| Cpd n° | Structure | Chemical name |
|---|---|---|
| 1 | 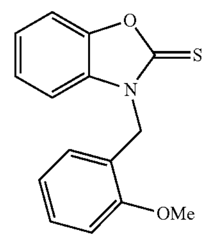 | 3-(2-methoxybenzyl)benzo[d]oxazole-2(3H)-thione |
| 2 | 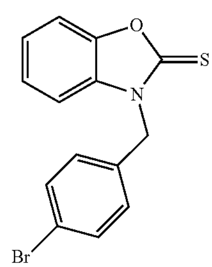 [SMILES: S=c1oc2ccccc2n1Cc1ccc(Br)cc1] | 3-(4-bromobenzyl)benzo[d]oxazole-2(3H)-thione |
| 4 | 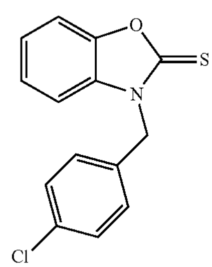 [SMILES: S=c1oc2ccccc2n1Cc1ccc(Cl)cc1] | 3-(4-chlorobenzyl)benzo[d]oxazole-2(3H)-thione |
| 5 | 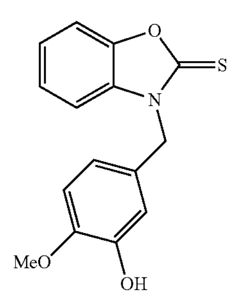 [SMILES: COc1ccc(Cn2c(=S)oc3ccccc32)cc1O] | 3-(3-hydroxy-4-methoxybenzyl)benzo[d]oxazole-2(3H)-thione |

| Cpd n° | Structure | Chemical name |
|---|---|---|
| 6 | 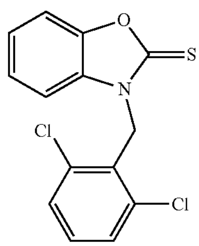 [SMILES: S=c1oc2ccccc2n1Cc1c(Cl)cccc1Cl] | 3-(2,6-dichlorobenzyl)benzo[d]oxazole-2(3H)-thione |
| 7 | 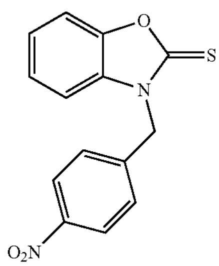 [SMILES: O=[N+]([O-])c1ccc(Cn2c(=S)oc3ccccc32)cc1] | 3-(4-nitrobenzyl)benzo[d]oxazole-2(3H)-thione |
| 9 | 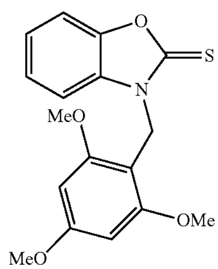 [SMILES: COc1cc(OC)c(Cn2c(=S)oc3ccccc32)c(OC)c1] | 3-(2,4,6-trimethoxybenzyl)benzo[d]oxazole-2(3H)-thione |
| 10 | 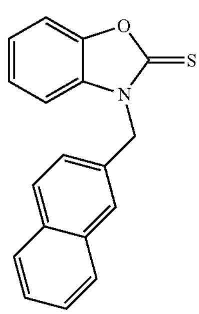 [SMILES: S=c1oc2ccccc2n1Cc1ccc2ccccc2c1] | 3-(naphthalen-2-ylmethyl)benzo[d]oxazole-2(3H)-thione |
| 11 | 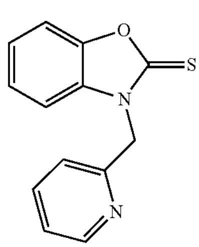 [SMILES: S=c1oc2ccccc2n1Cc1ccccn1] | 3-(pyridin-2-ylmethyl)benzo[d]oxazole-2(3H)-thione |
| 12 |  | 3-(3-methoxybenzyl)benzo[d]oxazole-2(3H)-thione |
| 13 |  | 3-(4-fluorobenzyl)benzo[d]oxazole-2(3H)-thione |
| 14 |  | 3-(4-(trifluoromethyl)benzyl)benzo[d]oxazole-2(3H)-thione |
| 15 |  | 3-(2-fluorobenzyl)benzo[d]oxazole-2(3H)-thione |
| 16 |  | 3-(3-fluorobenzyl)benzo[d]oxazole-2(3H)-thione |

| Cpd n° | Structure | Chemical name |
|---|---|---|
| 17 | 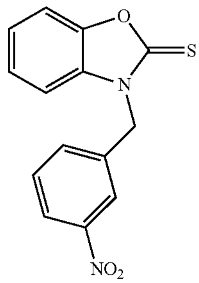 [SMILES: O=[N+]([O-])c1cccc(Cn2c(=S)oc3ccccc32)c1] | 3-(3-nitrobenzyl)benzo[d]oxazole-2(3H)-thione |
| 18 | 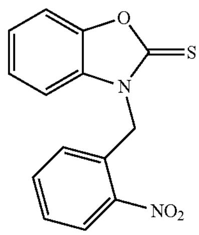 [SMILES: O=[N+]([O-])c1ccccc1Cn1c(=S)oc2ccccc21] | 3-(2-nitrobenzyl)benzo[d]oxazole-2(3H)-thione |
| 19 | 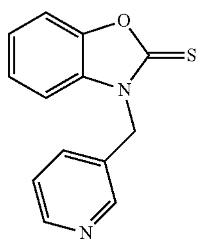 [SMILES: S=c1oc2ccccc2n1Cc1cccnc1] | 3-(pyridin-3-ylmethyl)benzo[d]oxazole-2(3H)-thione |
| 21 | 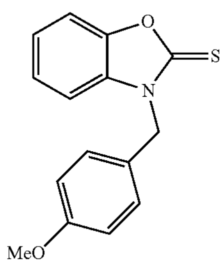 [SMILES: COc1ccc(Cn2c(=S)oc3ccccc32)cc1] | 3-(4-methoxybenzyl)benzo[d]oxazole-2(3H)-thione |
| 22 | 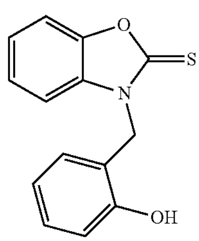 [SMILES: Oc1ccccc1Cn1c(=S)oc2ccccc21] | 3-(2-hydroxybenzyl)benzo[d]oxazole-2(3H)-thione |
| 23 | 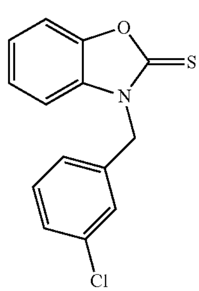 [SMILES: S=c1oc2ccccc2n1Cc1cccc(Cl)c1] | 3-(3-chlorobenzyl)benzo[d]oxazole-2(3H)-thione |
| 24 | | 3-(2-chlorobenzyl)benzo[d]oxazole-2(3H)-thione |
| 25 | | 3-(3-hydroxybenzyl)benzo[d]oxazole-2(3H)-thione |
| 26 | | 3-((1H-indol-2-yl)methyl)benzo[d]oxazole-2(3H)-thione |
| 27 | | 3-((1H-pyrrol-2-yl)methyl)benzo[d]oxazole-2(3H)-thione |
| 29 | | 3-((1H-indol-4-yl)methyl)benzo[d]oxazole-2(3H)-thione |

| Cpd n° | Structure | Chemical name |
|---|---|---|
| 30 | | 3-((1H-indazol-4-yl)methyl)benzo[d]oxazole-2(3H)-thione |
| 31 | | 3-((1H-indazol-5-yl)methyl)benzo[d]oxazole-2(3H)-thione |
| 32 | | 3-((1H-indol-6-yl)methyl)benzo[d]oxazole-2(3H)-thione |
| 33 | | 3-(quinolin-4-ylmethyl)benzo[d]oxazole-2(3H)-thione |
| 35 | | 1-(2-hydroxybenzyl)-1H-benzo[d]imidazole-2(3H)-thione |
| 36 | 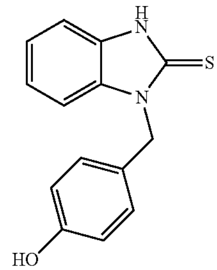 [SMILES: Oc1ccc(Cn2c(=S)[nH]c3ccccc32)cc1] | 1-(4-hydroxybenzyl)-1H-benzo[d]imidazole-2(3H)-thione |
| 37 | 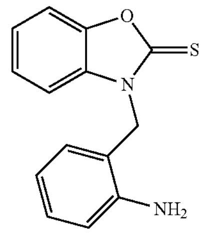 | 3-(2-aminobenzyl)benzo[d]oxazole-2(3H)-thione |
| 38 | 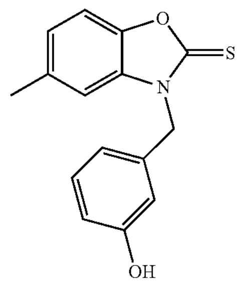 [SMILES: Cc1ccc2oc(=S)n(Cc3cccc(O)c3)c2c1] | 3-(3-hydroxybenzyl)-5-methylbenzo[d]oxazole-2(3H)-thione |
| 39 | 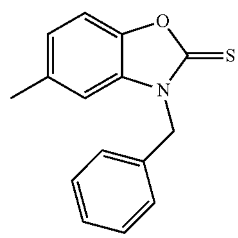 [SMILES: Cc1ccc2oc(=S)n(Cc3ccccc3)c2c1] | 3-benzyl-5-methylbenzo[d]oxazole-2(3H)-thione |
| 41 | 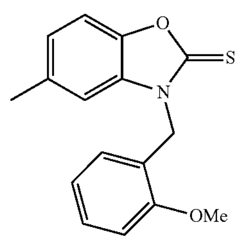 [SMILES: COc1ccccc1Cn1c(=S)oc2ccc(C)cc21] | 3-(2-methoxybenzyl)-5-methylbenzo[d]oxazole-2(3H)-thione |
| 42 | 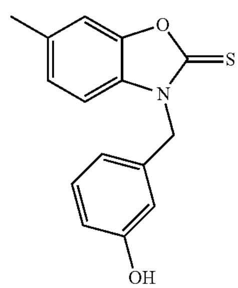 [SMILES: Cc1ccc2c(c1)oc(=S)n2Cc1cccc(O)c1] | 3-(3-hydroxybenzyl)-6-methylbenzo[d]oxazole-2(3H)-thione |

-continued

| Cpd n° | Structure | Chemical name |
|---|---|---|
| 43 | 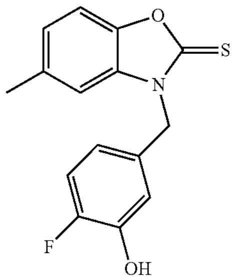 [SMILES: Cc1ccc2oc(=S)n(Cc3ccc(F)c(O)c3)c2c1] | 3-(4-fluoro-3-hydroxybenzyl)-5-methylbenzo[d]oxazole-2(3H)-thione |
| 44 | | 3-(4-fluoro-3-hydroxybenzyl)-5-(trifluoromethyl)benzo[d]oxazole-2(3H)-thione | or pharmaceutically acceptable enantiomers, salts and solvates thereof.

The compounds of table 1 were named using ChemBioDraw® Ultra version 12.0 (PerkinElmer).

The compounds of Formula I and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the present invention may be administered in the form of pharmaceutically acceptable salts.

The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl) aminomethane, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:
(i) by reacting the compound of Formula I with the desired acid;
(ii) by reacting the compound of Formula I with the desired base;
(iii) by removing an acid- or base-labile protecting group from a suitable precursor of the compound of Formula I or by ring-opening a suitable cyclic precursor, for example, a lactone or lactam, using the desired acid; or
(iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

All references to compounds of Formula I include references to enantiomers, salts, solvates, polymorphs, multi-component complexes and liquid crystals thereof.

The compounds of the invention include compounds of Formula I as hereinbefore defined, including all polymorphs and crystal habits thereof, prodrugs and isomers thereof (including optical, geometric and tautomeric isomers) and isotopically-labeled compounds of Formula I.

The invention also generally covers all pharmaceutically acceptable predrugs and prodrugs of the compounds of Formula I.

Process for Manufacturing Compounds of the Invention

The compounds of Formula I can be prepared by different ways with reactions known to a person skilled in the art.

The present invention further relates to a process of manufacturing the compounds of Formula I of the invention.

According to an embodiment, the process of the invention comprises:

a) reacting a compound of formula (i)

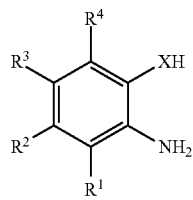

wherein X, $R^1$, $R^2$, $R^3$, $R^4$ are as defined in Formula I; with a compound of formula (ii)

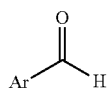

wherein Ar is as defined in Formula I;
so as to obtain a compound of formula (iv)

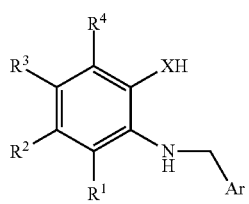

wherein Ar, X, $R^1$, $R^2$, $R^3$ and $R^4$ are as defined above;

b) reacting a compound of formula (iv) with carbon disulfide so as to obtain a compound of Formula I

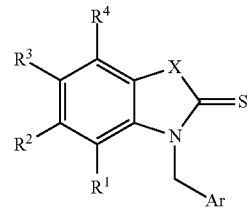

wherein Ar, X, $R^1$, $R^2$, $R^3$ and $R^4$ are as defined above.

According to one embodiment, compounds of formula (iv) may be prepared by direct reductive amination of compound of formula (i) and (ii) in a one-pot reaction as reported by Abdel-Magid et al. in J. Org. Chem., 1996, 61, 3849-3862. In this embodiment, reductive amination is preferably conducted in presence of $NaBH(OAc)_3$.

According to an alternative embodiment, the process of the invention comprises:

a1) reacting a compound of formula (i)

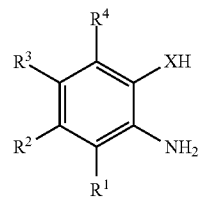

wherein X, $R^1$, $R^2$, $R^3$, $R^4$ are as defined in Formula I; with a compound of formula (ii)

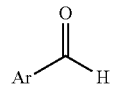

wherein Ar is as defined in Formula I;
so as to obtain a compound of formula (iii)

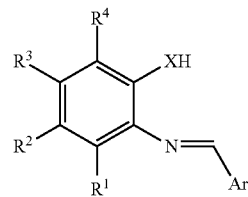

wherein Ar, X, R1, R2, R3 and R4 are as defined above;
a2) reacting a compound of formula (iii) with a reducing agent so as to obtain a compound of formula (iv)

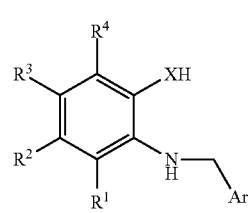

wherein Ar, X, $R^1$, $R^2$, $R^3$ and $R^4$ are as defined above;

b) reacting a compound of formula (iv) with carbon disulfide so as to obtain a compound of Formula I

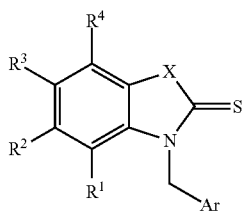

wherein Ar, X, $R^1$, $R^2$, $R^3$ and $R^4$ are as defined above.

According to one embodiment, the process of the invention is particularly adapted in the case wherein X represents O.

According to an embodiment, step a1) comprises reacting compounds (i) and (ii) in presence of $MgSO_4$ or $Na_2SO_4$, preferably anhydrous $MgSO_4$. According to an alternative embodiment, step a) comprises reacting compounds (i) and (ii) in the absence of $MgSO_4$ or $Na_2SO_4$.

In step a1) the solvent is preferably selected from tetrahydrofurane, ethanol, methanol, dichloroethane. Preferably, step a) is conducted at room temperature.

In one embodiment, compound (iii) obtained in step a1) may be used without further purification in step a2).

According to an embodiment, the reducing agent used in step a2) is selected from sodium borohydride, $NaBH_3CN$, $NaBH(OAc)_3$, preferably the reducing agent is sodium borohydride. In step a2) the solvent is preferably selected from tetrahydrofurane, dichloroethane. Preferably, step a2) is conducted at a temperature ranging from 0° C. to room temperature.

In one embodiment, compound (iv) obtained in step a2) may be used without further purification in step b).

According to an embodiment, step b) comprises reacting compound of formula (iv) with carbon disulfide in presence of KOH. In step b) the solvent is preferably selected from EtOH, MeOH, water or a mixture thereof. Preferably, step b) is conducted at a temperature ranging from 0° C. to room temperature, or solvent reflux, preferably at solvent reflux.

According to a preferred embodiment, compound of Formula I is purified by precipitation.

In general, the synthesis pathways for any individual compound of Formula I will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the Formula I and related formulae can furthermore be obtained by liberating compounds of the Formula I from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Use of the Compounds of the Invention

The present invention further relates to the use of the compounds of the invention or pharmaceutically acceptable enantiomers, salts and solvates thereof for the treatment of disorders, diseases or conditions related to MIF. In a specific embodiment, the invention further relates to the use of the compounds of the invention or pharmaceutically acceptable enantiomers, salts and solvates thereof for the treatment of disorders, diseases or conditions related to MIF CD74 axis.

The present invention also relates to the compounds of the invention or pharmaceutically acceptable enantiomers, salts and solvates thereof for treating, or for use in the treatment of a disorder, a disease or a condition related to MIF.

The present invention also relates to a method for treating a disease or a disorder or a condition related to MIF comprising the administration of a therapeutically effective amount of the compounds of the invention or pharmaceutically acceptable enantiomers, salts and solvates thereof.

According to one embodiment, a disease or a disorder or a condition is related to MIF when MIF is overexpressed, compared to healthy subjects. MIF may be overexpressed in biological tissues and/or in biological fluids. Biological tissues may be for example tumor tissues. Biological fluids may be for example blood or serum. The determination of the concentration in MIF may be performed by means known by those skilled in the art, such as for example by enzyme-linked immunosorbent assay (ELISA).

In one embodiment, the disorder, disease or condition related to MIF is an inflammatory disease, an autoimmune disease, a metabolic disorder, a cancer or a cardiovascular and/or cerebrovascular disease.

Examples of inflammatory diseases include but are not limited to: acute inflammation, chronic inflammation, granulomatous inflammation, fibrinous inflammation, purulent inflammation, serous inflammation, ulcerative inflammation, systemic inflammation, sepsis, acne vulgaris, asthma, chronic prostatitis, glomerulonephritis, pelvic inflammatory disease, reperfusion injury, sarcoidosis, transplant rejection, neuropathic pain, fibromyalgia, colitis, inflammatory bowel disease, Crohn's disease, ulcerative colitis, Castleman's disease, ankylosing spondylitis, hepatitis, otitis, experimental allergic neuritis, organ transplant rejection, shock, spondylitis, diabetes mellitus type 2, sarcoidosis, meningitis, silicosis, acute respiratory distress syndrome, wet and dry age-related macular degeneration, fibrotic diseases, restenosis, interstitial cystitis, cerebral malaria, meningitis, interstitial cystitis, gout, traumatic arthritis, rubella arthritis, acute synovitis, silicosis, muscle degeneration, diabetic retinopathy, macular degeneration, rhinovirus infection, peroral disease, such as gingivitis and periodontitis, eczema, contact dermatitis, psoriasis, and conjunctivitis.

Examples of autoimmune diseases include but are not limited to: celiac disease, rheumatoid arthritis, juvenile rheumatoid arthritis, vasculitis, psoriasis, psoriatic arthritis, multiple sclerosis, autoimmune uveitis, ankylosing spondylitis, Pemphigus, Myasthenia gravis, Guillain-Barre syndrome, hepatitis, autoimmune glomerulonephritis, systemic lupus erythematosus, lupus nephritis, diabetes mellitus type 1, Reiter's syndrome, polymyositis, graft versus host disease.

Examples of metabolic disorders include but are not limited to: obesity, steroid-resistance, glucose intolerance, metabolic syndrome.

Examples of cancers include but are not limited to: angiogenesis, multiple myeloma, leukemia, lymphoma, Hodgkin's disease, cancer of the bone, mouth/pharynx, oesophagus, larynx, stomach, intestine, colon, rectum, liver, pancreas, nerve, brain, head and neck, throat, ovary, uterus, prostate, testis, bladder, kidney, breast, non-melanoma, skin cancer, teratoma, rhabdomyosarcoma, glioma, metastatic bone disease and other forms of metastasis.

Examples of cardiovascular and/or cerebrovascular disease includes but are not limited to: atherosclerosis, restenosis of an atherosclerotic coronary artery, acute coronary syndrome, myocardial infarction, cardiac-allograft vasculopathy, stroke, ischemic and hemorrhagic stroke, neurotrauma/closed head injury, cardiac reperfusion injury.

Examples of MIF related diseases, preferably MIF/CD74 related diseases, disorders or conditions include but are not limited to: acute inflammation, chronic inflammation, granulomatous inflammation, fibrinous inflammation, purulent inflammation, serous inflammation, ulcerative inflammation, systemic inflammation, sepsis, acne vulgaris, asthma, celiac disease, chronic prostatitis, glomerulonephritis, pelvic inflammatory disease, reperfusion injury, rheumatoid arthritis, sarcoidosis, transplant rejection, vasculitis, interstitial cystitis, inflammatory myopathies, systemic sclerosis, and include dermatomyositis, polymyositis, inclusion body myositis, psoriatic arthritis, Reiter's syndrome, gout, traumatic arthritis, rubella arthritis and acute synovitis, rheumatoid spondylitis, osteoarthritis, gouty arthritis and other arthritic conditions, septic shock, endotoxic shock, gram negative sepsis, toxic shock syndrome, Alzheimer's disease, stroke, ischemic and hemorrhagic stroke, neurotrauma/closed head injury, atherosclerosis, asthma, acute respiratory distress syndrome, meningitis, silicosis, restenosis of an atherosclerotic coronary artery, acute coronary syndrome, myocardial infarction, cardiac-allograft vasculopathy, restenosis, cardiac reperfusion injury, brain and renal reperfusion injury, chronic renal failure, thrombosis, diabetic retinopathy, macular degeneration, inflammatory bowel disease, Crohn's disease, ulcerative colitis, multiple sclerosis, muscle degeneration, diabetic retinopathy, macular degeneration, rhinovirus infection, peroral disease, such as gingivitis and periodontitis, eczema, contact dermatitis, psoriasis, and conjunctivitis; angiogenesis, multiple myeloma, leukemia, lymphoma, Hodgkin's disease, cancer of the bone, mouth/pharynx, oesophagus, larynx, stomach, intestine, colon, rectum, liver, pancreas, nerve, brain, head and neck, throat, ovary, uterus, prostate, testis, bladder, kidney, breast, non-melanoma, skin cancer, teratoma, rhabdomyosarcoma, glioma, metastatic bone disease and other forms of metastasis.

In one embodiment, the disorder, disease or condition related to MIF is colorectal cancer, prostate cancer, sepsis, endometriosis, colitis, breast carcinoma, hepatocellular carcinoma, lung adenocarcinoma, melanoma, colon cancer, nasopharyngeal carcinoma, esophageal cancer, systemic inflammation (including polymicrobial sepsis, arthritis and autoimmune diabetes), asthma, viral infection, rheumatoid arthritis, inflammatory bowel disease or atherosclerosis.

In one embodiment, the disorder, disease or condition related to MIF is colorectal cancer, prostate cancer, sepsis, endometriosis or colitis.

In one embodiment, the disorder, disease or condition related to MIF is rheumatoid arthritis, multiple sclerosis, psoriasis, Crohn's disease, ulcerative colitis, systemic lupus erythematosus, endometriosis, sepsis, prostate cancer. In one embodiment, the disorder, disease or condition related to MIF is rheumatoid arthritis. In one embodiment, the disorder, disease or condition related to MIF is multiple sclerosis. In one embodiment, the disorder, disease or condition related to MIF is psoriasis. In one embodiment, the disorder, disease or condition related to MIF is Crohn's disease. In one embodiment, the disorder, disease or condition related to MIF is ulcerative colitis. In one embodiment, the disorder, disease or condition related to MIF is systemic lupus erythematosus. In one embodiment, the disorder, disease or condition related to MIF is endometriosis. In one embodiment, the disorder, disease or condition related to MIF is sepsis. In one embodiment, the disorder, disease or condition related to MIF is prostate cancer.

The present invention further relates to the use of the compounds of the invention or pharmaceutically acceptable enantiomers, salts and solvates thereof as inhibitors of MIF. Accordingly, in a particularly preferred embodiment, the invention relates to the use of compounds of Formula I and subformulae in particular those of table 1 above, or pharmaceutically acceptable enantiomers, salts and solvates thereof, as inhibitors of MIF. Accordingly, the invention relates to the use of these compounds or enantiomers, salts and solvates thereof for the synthesis of pharmaceutical active ingredients, such as inhibitors of MIF.

According to a specific embodiment, the invention relates to the use of the compounds of the invention or pharmaceutically acceptable enantiomers, salts and solvates thereof as inhibitors of MIF by inhibiting MIF binding to CD74, and/or CXCRs (including CXCR2, CXCR4, CXCR7).

According to a further feature of the present invention there is provided a method for inhibiting MIF, in a subject, preferably a warm blooded animal, and even more preferably a human, in need of such treatment, which comprises administering to said patient an effective amount of compound of the present invention, or a pharmaceutically acceptable enantiomer, salt and solvate thereof.

In one embodiment, compounds of the invention or pharmaceutically acceptable enantiomers, salts or solvates thereof are for use in the treatment of disorders, diseases or conditions related to MIF.

The invention further relates to a method for treatment of disorders, diseases or conditions related to MIF, which comprises administering to a mammalian species in need thereof a therapeutically effective amount of the compound according to the invention or a pharmaceutically acceptable enantiomers, salts or solvates thereof.

The invention also provides for a method for delaying in subject the onset of disorders, diseases or conditions related to MIF, comprising the administration of a pharmaceutically effective amount of a compound of Formula I or pharmaceutically acceptable enantiomer, salt and solvate thereof to a subject in need thereof.

Preferably, the subject is a warm-blooded animal, more preferably a human.

In another embodiment, the present invention is directed to the treatment of a disease associated with MIF, comprising administering an effective amount of a pharmaceutical composition comprising one or more compound of the present invention, or a pharmaceutically acceptable enantiomer, salt and solvate thereof, to a subject in need thereof.

The compounds of the invention are therefore useful as medicaments, in particular in the treatment of disorders, diseases or conditions related to MIF. The invention further provides the use of a compound of Formula I or a pharmaceutically acceptable enantiomer, salt and solvate thereof for the manufacture of a medicament for treating and/or preventing disorders, diseases or conditions related to MIF.

The present invention also relates to a method for inhibiting MIF, thereby inhibiting inflammation (such as, for example, by inhibiting ERK/MAPK or Src pathway or by inhibiting the release of inflammatory cytokines IL-1, IL-2, IL-6, IL-8, IFN-γ and TNFα).

The present invention also relates to a method for inhibiting MIF, thereby inhibiting cell proliferation and/or tumor growth and/or angiogenesis in a subject in need thereof.

The present invention also relates to a method for modulating the biological activity of MIF, such as, for example, inhibiting the effect of MIF on a cell (for example thereby inhibiting intracellular signalling pathways associated with MIF and CD74).

Technics to measure MIF biological activities are well known to the person skilled in the art. Examples of such assays include but are not limited to: 4-hydroxyphenylpyruvate Tautomerase Assays, Dopachrome Tautomerase Assays, MIF enzymatic activity, MIF immunoregulatory activities, MIF glucocorticoid regulating activity, MIF binding to target cells, inhibition of MIF release or synthesis, inhibition of MIF immunoreactivity with MIF-specific antibodies, alterations of MIF conformation or structural integrity as assessed by circular dichroism spectroscopy, liquid NMR-spectroscopy, X-ray crystallography, thermal stability measurement, inhibition of the pro-proliferative effects of MIF on quiescent, non-quiescent cells and inhibition of the associated prolonged ERK activation therein, inhibition of MIF-induced arachadonic acid release from cells, inhibition of MIF-induced fructose 2,6 bisphosphate formation in L6 myocytes, inhibition of MIF toxicity in the MIF, TNF, or LPS-challenged test animals, inhibition of the glucocorticoid counter-regulatory activity of MIF in vitro or in vivo, inhibition of the MIF-induced functional inactivation of the p53 tumor suppressor protein, inhibition of MIF-induced release of prostaglandin E2, and inhibition of morbidity or mortality in any of a number of animal models of human diseases that are characterized by the release, production and/or appearance of MIF.

The present invention also relates to a method for inhibiting the interaction between MIF and CD74, comprising administering a compound of the invention or pharmaceutically acceptable enantiomers, salts and solvates thereof, thereby treating diseases related to MIF CD74 axis in a subject in need thereof.

The present invention also relates to a method for inhibiting inflammation, comprising administering a compound of the invention or pharmaceutically acceptable enantiomers, salts and solvates thereof, thereby treating diseases related to MIF in a subject in need thereof.

The present invention also relates to a method for inhibiting cell proliferation and/or tumor growth and/or angiogenesis, comprising administering a compound of the invention or pharmaceutically acceptable enantiomers, salts and solvates thereof, thereby treating diseases related to MIF in a subject in need thereof.

The present invention also relates to a method for inhibiting vasoconstriction, comprising administering a compound of the invention or pharmaceutically acceptable enantiomers, salts and solvates thereof, thereby treating diseases related to MIF in a subject in need thereof.

According to a specific embodiment, compounds of the invention or pharmaceutically acceptable enantiomers, salts and solvates thereof are useful in veterinary field.

In one embodiment, the subject is affected with, preferably is diagnosed with a disorder, a disease or a condition related to MIF, preferably to MIF CD74 axis.

In another embodiment, the subject is at risk of developing a disorder, a disease or a condition related to MIF. In one embodiment of the invention, the subject presents a non-genetic predisposition to a disorder, a disease or a condition related to MIF CD74 axis. In one embodiment of the invention, the subject has a genetic or familial predisposition to a disorder, a disease or a condition related to MIF.

The invention also provides pharmaceutical compositions comprising or consisting of a compound of Formula I or a pharmaceutically acceptable enantiomer, salt and solvate thereof and at least one pharmaceutically acceptable carrier, diluent, excipient and/or adjuvant. The invention also covers pharmaceutical compositions which contain, in addition to a compound of the present invention, a pharmaceutically acceptable enantiomer, salt and solvate thereof as active ingredient, additional therapeutic agents and/or active ingredients. According to one embodiment, the composition of the invention may further comprise, in addition to the compounds of the invention, at least one additional compound, including another MIF inhibitors.

Another object of this invention is a medicament comprising or consisting of at least one compound of the invention, or a pharmaceutically acceptable enantiomer, salt and solvate thereof, as active ingredient.

Generally, for pharmaceutical use, the compounds of the invention may be formulated as a pharmaceutical preparation comprising at least one compound of the invention or a pharmaceutically acceptable enantiomer, salt and solvate thereof and at least one pharmaceutically acceptable carrier, diluent, excipient and/or adjuvant, and optionally one or more further pharmaceutically active compounds.

In one embodiment, the pharmaceutical composition or the medicament of the invention comprises at least one compound of the invention or a pharmaceutically acceptable enantiomer, salt and solvate thereof as unique pharmaceutically active compound.

In one embodiment, a therapeutically effective amount of the composition, the pharmaceutical composition or the medicament of the invention is administered or is to be administered alone, i.e. is not administered in combination with another therapeutic agent for treating a disease, or disorder or a condition.

In another embodiment, the composition, the pharmaceutical composition or the medicament of the present invention is administered or is to be administered with other active agents. In one embodiment, the composition, the pharmaceutical composition or the medicament and the other active agent may be administered separately or in conjunction.

In one embodiment, the composition, the pharmaceutical composition or the medicament of the invention is for curing disorders, diseases or conditions related to MIF.

In another embodiment, the composition, the pharmaceutical composition or the medicament of the invention slows down or stops the progression, aggravation, or deterioration of one or more symptoms of disorders, diseases or conditions related to MIF; bringing about ameliorations of the symptoms of disorders, diseases or conditions related to MIF; reducing the severity or incidence of disorders, diseases or conditions related to MIF.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, liposomes, nanoparticles, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

In another embodiment of the invention, the administration dose of the composition, the pharmaceutical composition or the medicament is determined by the skilled artisan and personally adapted to each subject and/or the severity of the disease.

EXAMPLES

The present invention is further illustrated by the following examples.

I. Chemistry Examples

I.1. Material

Tetrahydrofuran was distilled from sodium and benzophenone. Methanol was distilled from magnesium turnings. Analytical TLC was performed on precoated Merck 60 $F_{254}$ glass plates and visualized by exposure to ultraviolet light (254 nm) or by using solution of 20% phosphomolybdic acid in EtOH or vanillin/sulfurinc acid/acetic acid in EtOH. IR spectra were measured on a Bruker Vector 22 spectrophotometer (neat, $cm^{-1}$). $^1H$ and $^{13}C$ NMR spectra were recorded in $CDCl_3$ or DMSO-$d_6$ on a Bruker Avance 300 and chemical shifts are reported in ppm. The following abbreviations for multiplicity are used: m (multiplet), s (singlet), br s (broad singlet), d (doublet), t (triplet), dd (doublet of doublet), td (triplet of doublet), q (quadruplet).

I.2. General Method of Synthesis

N-(methyl aryl)-benzoxazol-2-thiones were synthesized following a three-step synthetic pathway represented in the scheme below.

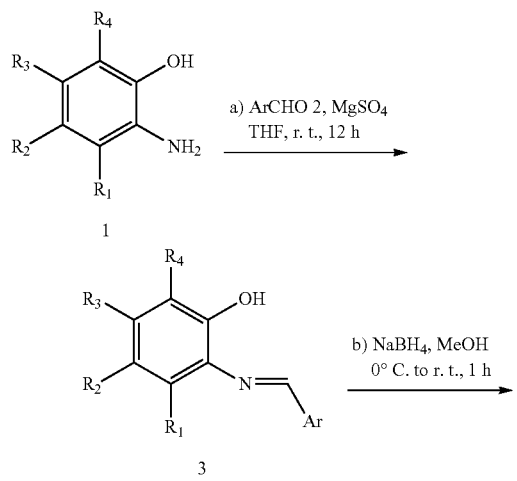

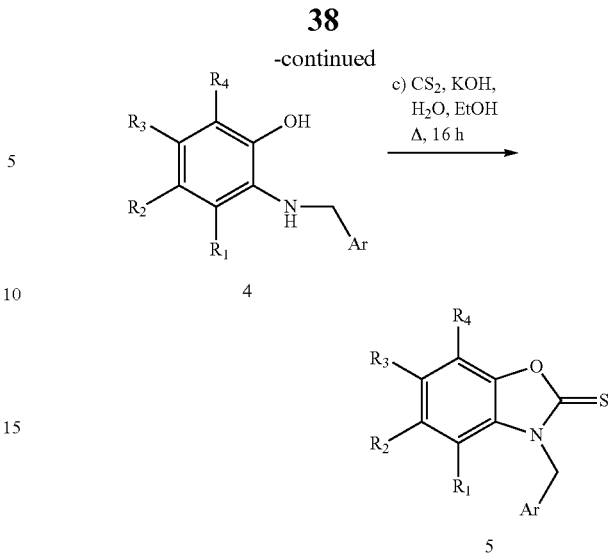

The synthesis begins by condensation of 2-aminophenol derivative 1 with various aldehydes 2. Subsequent reduction of resulting imine 3 with sodium borohydride, followed by cyclization of the resulting amino alcohol 4 with carbon disulfide leads to the N-(methyl aryl)-benzoxazol-2-thione 5 in good overall yield (60-90%). This three step sequence requires no purification of intermediate 3 and 4. A final purification by precipitation of 5 gives pure compounds.

The benzaldehyde derivative 2 (1 eq.) is added to a stirred mixture of aminophenol derivative 1 (1 eq.) and anhydrous $MgSO_4$ (4 eq.) in THF at room temperature. After 12 h of stirring, the mixture is filtered and the filtrate is concentrated to give the crude imine 3, which is used without further purification. Sodium borohydride (1.3 eq.) is added portionwise to a solution of the crude imine 3 in THF at 0° C. After the completion of the addition, the reaction mixture is maintained at room temperature for 30 min and then concentrated in vacuo. The reaction mixture is redissolved in EtOAc and washed with $H_2O$ (×2). The combined aqueous extracts are extracted with EtOAc (×3). The combined organic phases were washed with brine (×2), dried over $Na_2SO_4$ and concentrated to give the crude amino alcohol 4. KOH (0.5 eq.) and carbon disulfide (4 eq.) are added to a solution of the crude amino alcohol 4 in a mixture of EtOH/$H_2O$. The reaction mixture is heated at reflux for 16 h, then cooled to 0° C. Water is added to precipitate N-(methyl aryl)-benzoxazol-2-thione 5, which is recovered by filtration.

I.3. Products Characterizations

Compound 1: $^{13}C$ NMR (75 MHz, $CDCl_3$): 181.0; 157.0; 147.1; 132.0; 129.6; 129.3; 124.7; 124.1; 121.9; 120.8; 110.5; 110.3; 110.1; 55.4; 44.2. Yield: 86%.

Compound 2: $^{13}C$ NMR (75 MHz, $CDCl_3$): 180.9; 147.1; 132.9; 132.2 (2C); 131.4; 129.5 (2C); 125.0; 124.5; 122.5; 110.5; 109.7; 48.8. Yield: 74%.

Compound 4: $^{13}C$ NMR (75 MHz, $CDCl_3$): 181.0; 147.2; 134.5; 132.4; 131.5; 129.2 (2C); 129.1 (2C); 125.0; 124.5; 110.5; 109.7; 48.8. Yield: 72%.

Compound 5: $^{13}C$ NMR (75 MHz, $CDCl_3$): 180.8; 147.2; 146.6; 145.9; 131.6; 127.0; 124.8; 124.3; 119.7; 114.0; 110.8; 110.3; 110.0; 55.9; 49.1. Yield: 75%.

Compound 6: $^1H$ NMR (300 MHz, $CDCl_3$): 7.41-7.38 (m, 2H); 7.34-7.26 (m, 2H); 7.17 (td, J=1.2, 7.8 Hz, 1H); 7.06 (td, J=1.2, 8.1 Hz, 1H); 6.58 (d, J=8.1 Hz, 1H); 5.74 (s, 2H).

Compound 7: $^{13}$C NMR (75 MHz, DMSO-d$_6$): 179.9; 147.1; 146.5; 142.1; 131.2; 128.6 (2C); 125.3; 124.7; 123.8 (2C); 110.7; 110.4; 47.7. Yield: 70%.

Compound 9: $^{13}$C NMR (75 MHz, CDCl$_3$): 180.9; 153.6 (2C); 147.1; 138.1; 131.6; 129.5; 124.9; 124.4; 110.4; 109.9; 105.1 (2C); 60.8; 56.2 (2C); 49.7. Yield: 60%.

Compound 10: $^{13}$C NMR (75 MHz, CDCl$_3$): 181.1; 147.2; 133.1, 133.0; 131.7; 131.3; 129.1; 127.9; 127.8; 126.8; 126.6; 126.5; 125.2; 124.9; 124.4; 110.4; 110.0; 49.8.

Compound 11: $^{13}$C NMR (75 MHz, CDCl$_3$): 180.8; 153.8; 149.5; 147.1; 137.2; 131.8; 125.0; 124.4; 123.3; 122.7; 110.5; 110.2; 51.2. Yield: 32%.

Compound 12: $^{13}$C NMR (75 MHz, CDCl$_3$): 181.0; 160.0; 147.1; 135.4; 131.6; 130.0; 124.9; 124.3; 119.9; 113.7; 113.4; 110.3; 109.5; 55.2; 49.4. Yield: 70%.

Compound 13: $^1$H NMR (300 MHz, CDCl$_3$): 7.43-7.35 (m, 3H); 7.26-7.19 (m, 2H); 7.08-6.96 (m, 3H); 5.40 (s, 2H).

Compound 14: $^{13}$C NMR (75 MHz, CDCl$_3$): 7.62 (d, J=8.4 Hz, 2H); 7.50 (d, J=8.1 Hz, 2H); 7.40-7.37 (m, 1H); 7.29-7.20 (m, 2H); 6.97-6.94 (m, 1H); 5.49 (s, 2H).

Compound 15: $^1$H NMR (300 MHz, CDCl$_3$): 7.51 (td, J=1.5, 7.5 Hz, 1H); 7.38-7.20 (m, 4H); 7.14-7.07 (m, 3H); 5.50 (s, 2H).

Compound 16: $^{13}$C NMR (75 MHz, CDCl$_3$): 181.0. 162,9 (d, J=246 Hz); 147.1; 136.2 (d, J=7.5 Hz); 131.4; 130.6 (d, J=8.2 Hz); 125.0; 124.5; 123.3 (d, J=2.2 Hz); 115.5 (d, J=21.0 Hz); 114.7 (d, J=22.5 Hz); 110.5; 109.7; 48.8.

Compound 17: $^{13}$C NMR (75 MHz, DMSO-d$_6$): 179.9; 147.9; 146.5; 136.7; 134.1; 131.2; 130.3; 125.3; 124.7; 123.0; 122.6; 110.7; 110.4; 47.5. Yield: 75%.

Compound 18: $^{13}$C NMR (75 MHz, CDCl$_3$): 181.3; 147.9; 147.2; 134.2; 131.6; 129.5; 129.0; 127.7; 125.7; 125.3; 124.8; 110.7; 109.5; 46.5. Yield: 75%.

Compound 19: $^{13}$C NMR (75 MHz, CDCl$_3$): 180.9; 150.0; 149.2; 147.2; 135.7; 131.3; 129.9; 125.1; 124.6; 123.9; 110.6; 109.5; 46.9. Yield: 78%.

Compound 21: $^{13}$C NMR (75 MHz, CDCl$_3$): 180.7; 159.6; 147.2; 131.6; 129.3 (2C); 125.9; 124.9; 124.3; 114.3 (2C); 110.4; 110.0; 55.3; 49.1. Yield: 70%.

Compound 22: $^{13}$C NMR (75 MHz, DMSO-d$_6$): 179.8; 155.0; 146.4; 131.5; 129.1, 128.4; 125.0; 124.3; 120.3; 119.1; 115.3; 110.8; 110.1; 43.9. Yield: 80%.

Compound 23: $^{13}$C NMR (75 MHz, CDCl$_3$): 181.0; 147.2; 135.8; 134.9; 131.4; 130.3; 128.7; 125.8; 125.1; 124.5; 110.5; 109.7; 48.8. Yield: 78%.

Compound 24: $^{13}$C NMR (75 MHz, CDCl$_3$): 181.3; 147.2; 132.9; 131.5; 131.3; 129.9; 129.5; 128.4; 127.4; 125.1; 124.5; 110.4; 109.9; 46.6. Yield: 85%.

Compound 25: $^{13}$C NMR (75 MHz, DMSO-d$_6$): 179.8; 157.6; 146.4; 135.8; 131.3; 129.8; 125.2; 124.5; 118.1; 115.0; 114.1; 110.9; 110.3; 48.3. Yield: 80%.

Compound 26: $^{13}$C NMR (75 MHz, DMSO-d$_6$): 179.6; 146.5; 136.2; 131.7; 131.3; 127.6; 125.1; 124.4; 121.4; 119.9; 119.2; 111.4; 110.8; 110.2; 101.0; 42.9. Yield: 85%.

Compound 27: $^{13}$C NMR (75 MHz, DMSO-d$_6$): 179.2; 146.4; 131.1; 125.0; 124.3; 123.7; 118.4; 110.8; 110.1; 108.2; 107.9; 42.5. Yield: 50%.

Compound 29: $^{13}$C NMR (75 MHz, DMSO-d$_6$): 179.6; 146.4; 135.5; 131.3; 127.6; 126.1; 125.1; 124.9; 124.4; 120.9; 119.8; 111.7; 111.1; 110.7; 101.13; 49.18.

Compound 30: $^{13}$C NMR (75 MHz, DMSO-d$_6$): 179.7; 146.5; 139.5; 133.6; 131.2; 126.5; 125.9; 125.2; 124.5; 122.7; 120.0; 111.0; 110.6; 110.3; 48.7.

Compound 31: $^{13}$C NMR (75 MHz, DMSO-d$_6$): 179.8; 146.5; 139.8; 133.4; 132.5; 131.3; 125.2; 124.6; 122.5; 121.1; 120.1; 110.9; 110.3; 109.0; 48.7.

Compound 32: $^{13}$C NMR (75 MHz, CDCl$_3$): 180.1; 147.3; 134.2; 131.5; 128.7; 125.2; 125.0; 124.8; 123.9; 122.1; 119.2; 116.2; 111.0; 110.5; 102.6; 49.1.

Compound 33: $^{13}$C NMR (75 MHz, DMSO-d$_6$): 180.1; 150.3; 147.6; 146.7; 139.5; 131.6; 129.7 (2C); 127.1; 125.5; 125.4; 124.8; 123.5; 117.7; 110.8; 110.5; 45.9.

Compound 35: $^{13}$C NMR (75 MHz, DMSO-d$_6$): 168.9; 154.6; 132.4; 130.8; 128.4; 127.8; 122.9; 122.2; 122.1; 119.0; 115.2; 109.7; 109.6; 40.9.

Compound 36: $^{13}$C NMR (75 MHz, DMSO-d$_6$): 168.6; 156.8; 132.2; 130.8; 129.1 (2C); 126.6; 122.9; 122.2; 115.2 (2C); 109.9; 109.7; 45.7.

Compound 37: $^{13}$C NMR (75 MHz, DMSO-d$_6$): 179.7; 146.5; 146.3; 131.2; 128.7; 128.1; 125.2; 124.5; 116.6; 116.3; 115.4; 111.1; 110.3; 45.8.

Compound 38: $^{13}$C NMR (75 MHz, DMSO-d$_6$): 179.9; 157.6; 144.7; 135.9; 135.0; 131.4; 129.8; 125.1; 119.0; 115.0; 114.0; 110.9; 109.9; 48.1; 20.9. Yield: 86%.

Compound 39: $^{13}$C NMR (75 MHz, CDCl$_3$): 181.1; 145.4; 135.2; 134.0; 131.7; 129.0 (2C); 128.3; 127.6 (2C); 125.0; 110.2; 109.9; 49.4; 21.5.

Compound 41: $^{13}$C NMR (75 MHz, CDCl$_3$): 181.2; 156.9; 145.3; 134.9; 132.0; 129.5; 128.9; 124.8; 122.0; 120.8; 110.6; 110.5; 109.7; 55.3; 44.0; 21.5.

Compound 42: $^{13}$C NMR (75 MHz, DMSO-d$_6$): 179.5; 157.6; 146.6; 135.8; 134.6; 129.7; 129.1; 125.8; 118.1; 114.9; 114.1; 110.5 (2C); 48.2; 20.8.

Compound 43: $^1$H NMR (300 MHz, DMSO-d$_6$): 9.92 (s, 1H); 7.45 (d, J=8.4 Hz, 1H); 7.23 (s, 1H); 7.14-7.08 (m, 2H); 6.99 (dd, J=2.1, 8.4 Hz, 1H); 6.89-6.83 (m, 1H); 5.34 (s, 2H); 2.35 (s, 3H).

Compound 44: $^1$H NMR (300 MHz, CDCl$_3$): 7.54 (dq, J=0.6, 8.4 Hz, 1H); 7.44 (d, J=8.4 Hz, 1H); 7.19-7.18 (m, 1H); 7.11-7.03 (m, 2H); 6.92-6.87 (m, 1H); 5.36 (s, 2H).

II. Biology Examples

II.1. MIF Tautomerase Assay Using 4-Hydroxyphenylpyruvate (4-HPP)

Method

Tautomerase activity was assessed using 4-hydroxyphenylpyruvate (4-HPP) as substrate. 4-HPP was dissolved in 50 mM ammonium acetate at pH 6.0, allowed to equilibrate to room temperature and stored at −20° C. 300 ng/mL of recombinant human MIF (rhMIF; RayBiotech, Le Perray en Yvelines, France) and tested compounds were pre-incubated at room temperature for 15 min. Tautomerase activity was assessed at room temperature, by adding 4-HHP to a 96-well plate containing 0.435 M boric acid at pH 6.6 and rhMIF with or without (positive control) tested compounds (1 nM), and by measuring the increase in absorbance at 320 nm over 10-360 s using the 2103 EnVision™ Multilabel Plate Readers (PerkinElmer, Villebon-sur-Yvette, France). Compounds were tested at 1 nM. The assay was replicated 3 times independently.

Tested Compounds

Compounds 38, 39 and 41 of the present invention were tested and compared to their respective "C=O" isosteres 38-O, 39-O and 41-O. Results are also compared to prototypical MIF inhibitor ISO-1.

Results

Results are presented in table 2 below and represent the percentage of MIF tautomerase activity inhibition as compared to the positive control with recombinant human MIF alone.

TABLE 2

Efficacies on tautomerase activity using 4-hydroxyphenylpyruvate (4-HPP)

| Cpd n° | Structure | tautomerase activity inhibition (%) |
|---|---|---|
| ISO-1 | (4-hydroxyphenyl-isoxazoline-methyl acetate) | 21 |
| 38 | (5-methyl-3-(3-hydroxybenzyl)-benzoxazole-2-thione) | 41 |
| 38-O | (5-methyl-3-(3-hydroxybenzyl)-benzoxazol-2-one) | 29 |
| 41 | (5-methyl-3-(2-methoxybenzyl)-benzoxazole-2-thione) | 36 |
| 41-O | (5-methyl-3-(2-methoxybenzyl)-benzoxazol-2-one) | 31 |
| 39 | (5-methyl-3-benzyl-benzoxazole-2-thione) | 35 |
| 39-O | (5-methyl-3-benzyl-benzoxazol-2-one) | 12 |
| 43 | (5-methyl-3-(3-fluoro-4-hydroxybenzyl)-benzoxazole-2-thione) | 39 |
| 44 | (5-trifluoromethyl-3-(3-fluoro-4-hydroxybenzyl)-benzoxazole-2-thione) | 43 |

Tested compound of the invention show a good inhibitory effect against the MIF tautomerase activity as compared to their corresponding benzoxazol-2-one analogues.

Tested compounds of the invention exhibit a highest or similar inhibitory effect against the MIF tautomerase activity as compared to the prototypical MIF inhibitor ISO-1.

The invention claimed is:

1. A compound of Formula I'

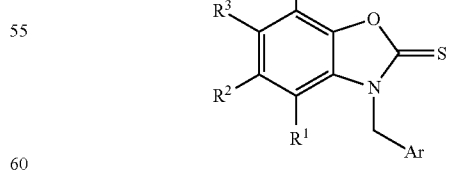

or a pharmaceutically acceptable enantiomer, salt or solvate thereof, wherein:

Ar represents an aryl or a heteroaryl group selected from the group consisting of indole, indazole, 7-azaindole, quinoline, quinolinone, dihydroquinolinone, dihydroquinaolinone, imidazole, pyrrole, pyrazol, benzimidazolone, benzoxazolone, benzimidazole-thione, benzotriazole, benimidazole, benzoxazinone, indolinedione, hydroxypyridinone and benzothiazolamine; optionally substituted by one or more substituents selected from the group consisting of halo, hydroxyl hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone; and $R^1$-$R^4$ are the same or different and represent a hydrogen atom or a group selected from the group consisting of hydroxyl, amino, nitro, cyano, carboxylic acid, alkyl, cycloalkyl, alkenyl, alkynyl, aryl, heteroaryl, hydroxyalkyl, alkoxy, C1-C8 acyl, and haloalkyl;

provided that compound of Formula I is not:
3-benzylbenzo[d]oxazole-2(3H)-thione;
3-(4-(dimethylamino)benzyl)benzo[d]oxazole-2(3H)-thione;
3-(2,4-dimethoxybenzyl)benzo[d]oxazole-2(3H)-thione;
3-(furan-2-ylmethyl)benzo[d]oxazole-2(3H)-thione;
3-(thiophen-2-ylmethyl)benzo[d]oxazole-2(3H)-thione;
3-(3,5-di-tert-butyl-4-hydroxybenzyl)benzo[d]thiazole-2(3H)-thione;
3-(5-(tert-butyl)-4-hydroxy-2-methylbenzyl)benzo[d]thiazole-2(3H)-thione;
3-(4-hydroxy-5-isopropyl-2-methylbenzyl)benzo[d]thiazole-2(3H)-thione;
3-(3-(tert-butyl)-2-hydroxy-5-methylbenzyl)benzo[d]thiazole-2(3H)-thione;
3-(3-allyl-4-hydroxy-5-methylbenzyl)benzo[d]thiazole-2(3H)-thione;
3-(4-hydroxy-3,5-diisopropylbenzyl)benzo[d]oxazole-2(3H)-thione;
3-(3,5-di-tert-butyl-4-hydroxybenzyl)benzo[d]oxazole-2(3H)-thione;
3-((2'-hydroxy-[1,1':3',1''-terphenyl]-5'-yl)methyl)benzo[d]oxazole-2(3H)-thione;
3-(3-(tert-butyl)-4-hydroxy-5-methylbenzyl)benzo[d]oxazole-2(3H)-thione;
3-(4-hydroxy-2,3,5-trimethylbenzyl)benzo[d]oxazole-2(3H)-thione;
3-(3,5-di-tert-butyl-2-hydroxybenzyl)benzo[d]oxazole-2(3H)-thione;
3-(2-hydroxy-3,5-dimethylbenzyl)benzo[d]oxazole-2(3H)-thione; or
3-((4'-hydroxy-[1,1':3',1''-terphenyl]-5'-yl)methyl)benzo[d]oxazole-2(3H)-thione.

2. The compound according to claim 1, having Formula Ia'

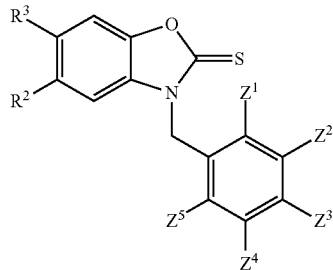

or a pharmaceutically acceptable enantiomer, salt or solvate thereof, wherein:

$Z^1$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring and a heterocyclyl, optionally substituted by one or more group selected from the group consisting of oxo, halo, hydroxyl, nitro, amino, alkoxy, alkyl, haloalkyl, alkenyl, alkynyl, aryl, and heteroaryl;

$Z^2$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^1$ or $Z^3$ an aryl ring, an heteroaryl ring, a cycloalkyl ring or a heterocyclyl, optionally substituted by one or more group selected from the group consisting of oxo, halo, hydroxyl, nitro, amino, alkoxy, alkyl, haloalkyl, alkenyl, alkynyl, aryl, and heteroaryl;

$Z^3$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^2$ or $Z^4$ an aryl ring, an heteroaryl ring, a cycloalkyl ring or a heterocyclyl, optionally substituted by one or more group selected from the group consisting of oxo, halo, hydroxyl, nitro, amino, alkoxy, alkyl, haloalkyl, alkenyl, alkynyl, aryl, and heteroaryl;

$Z^4$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^3$ or $Z^5$ an aryl ring, an heteroaryl ring, a cycloalkyl ring or a heterocyclyl, optionally substituted by one or more group selected from the group consisting of oxo, halo, hydroxyl, nitro, amino, alkoxy, alkyl, haloalkyl, alkenyl, alkynyl, aryl, and heteroaryl; and $Z^5$ represents a hydrogen atom or a group selected from the group consisting of halo, hydroxyl hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^4$ an aryl ring, an heteroaryl ring, a cycloalkyl ring or a heterocyclyl, optionally substituted by one or more group selected from the group consisting of: oxo, halo, hydroxyl, nitro, amino, alkoxy, alkyl, haloalkyl, alkenyl, alkynyl, aryl, and heteroaryl.

3. The compound according to claim 1, wherein $R^3$ represents H.

4. The compound according to claim 1, wherein said compound is selected from the group consisting of:
- 3-(2-methoxybenzyl)benzo[d]oxazole-2(3H)-thione;
- 3-(4-bromobenzyl)benzo[d]oxazole-2(3H)-thione;
- 3-(4-chlorobenzyl)benzo[d]oxazole-2(3H)-thione;
- 3-(3-hydroxy-4-methoxybenzyl)benzo[d]oxazole-2(3H)-thione;
- 3-(2,6-dichlorobenzyl)benzo[d]oxazole-2(3H)-thione;
- 3-(4-nitrobenzyl)benzo[d]oxazole-2(3H)-thione;
- 3-(2,4,6-trimethoxybenzyl)benzo[d]oxazole-2(3H)-thione;
- 3-(naphthalen-2-ylmethyl)benzo[d]oxazole-2(3H)-thione;
- 3-(3-methoxybenzyl)benzo[d]oxazole-2(3H)-thione;
- 3-(4-fluorobenzyl)benzo[d]oxazole-2(3H)-thione;
- 3-(4-(trifluoromethyl)benzyl)benzo[d]oxazole-2(3H)-thione;
- 3-(2-fluorobenzyl)benzo[d]oxazole-2(3H)-thione;
- 3-(3-fluorobenzyl)benzo[d]oxazole-2(3H)-thione;
- 3-(3-nitrobenzyl)benzo[d]oxazole-2(3H)-thione;
- 3-(2-nitrobenzyl)benzo[d]oxazole-2(3H)-thione;
- 3-(4-methoxybenzyl)benzo[d]oxazole-2(3H)-thione;
- 3-(2-hydroxybenzyl)benzo[d]oxazole-2(3H)-thione;
- 3-(3-chlorobenzyl)benzo[d]oxazole-2(3H)-thione;
- 3-(2-chlorobenzyl)benzo[d]oxazole-2(3H)-thione;
- 3-(3-hydroxybenzyl)benzo[d]oxazole-2(3H)-thione;
- 3-((1H-indol-2-yl)methyl)benzo[d]oxazole-2(3H)-thione;
- 3-((1H-pyrrol-2-yl)methyl)benzo[d]oxazole-2(3H)-thione;
- 3-((1H-indol-4-yl)methyl)benzo[d]oxazole-2(3H)-thione;
- 3-((1H-indazol-4-yl)methyl)benzo[d]oxazole-2(3H)-thione;
- 3-((1H-indazol-5-yl)methyl)benzo[d]oxazole-2(3H)-thione;
- 3-((1H-indol-6-yl)methyl)benzo[d]oxazole-2(3H)-thione;
- 3-(quinolin-4-ylmethyl)benzo[d]oxazole-2(3H)-thione;
- 1-(2-hydroxybenzyl)-1H-benzo[d]imidazole-2(3H)-thione;
- 1-(4-hydroxybenzyl)-1H-benzo[d]imidazole-2(3H)-thione;
- 3-(2-aminobenzyl)benzo[d]oxazole-2(3H)-thione;
- 3-(3-hydroxybenzyl)-5-methylbenzo[d]oxazole-2(3H)-thione;
- 3-benzyl-5-methylbenzo[d]oxazole-2(3H)-thione;
- 3-(2-methoxybenzyl)-5-methylbenzo[d]oxazole-2(3H)-thione;
- 3-(3-hydroxybenzyl)-6-methylbenzo[d]oxazole-2(3H)-thione;
- 3-(4-fluoro-3-hydroxybenzyl)-5-methylbenzo[d]oxazole-2(3H)-thione; and
- 3-(4-fluoro-3-hydroxybenzyl)-5-(trifluoromethyl)benzo[d]oxazole-2(3H)-thione.

5. The compound according to claim 1, being 3-(4-fluoro-3-hydroxybenzyl)-5-(trifluoromethyl)benzo[d]oxazole-2(3H)-thione.

6. A pharmaceutical composition comprising a compound according to claim 1, and at least one pharmaceutically acceptable carrier, diluent, excipient and/or adjuvant.

7. A method of treating a disorder, disease or condition related to MIF, comprising the administration to a patient in need thereof of a therapeutically effective amount of a compound according to claim 1 or a pharmaceutically acceptable enantiomer, salt or solvate thereof.

8. A method for inhibiting MIF in a patient in need thereof, comprising the administration to said patient of an effective amount of a compound according to claim 1, or a pharmaceutically acceptable enantiomer, salt and solvate thereof.

9. A process of manufacturing a compound according to claim 1, which comprises:

a) reacting a compound of formula (i')

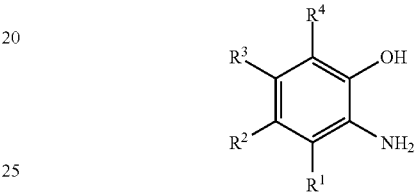

with a compound of formula (ii')

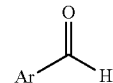

so as to obtain a compound of formula (iv')

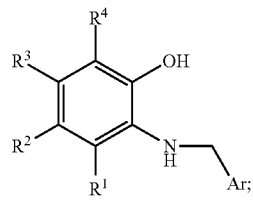

and b) reacting a compound of formula (iv') with carbon disulfide so as to obtain a compound of Formula I'

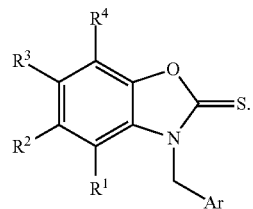

* * * * *